(12) United States Patent
Banerjee et al.

(10) Patent No.: US 6,949,557 B2
(45) Date of Patent: Sep. 27, 2005

(54) HYDROANTHRACENE BASED COMPOUNDS AS ANTICANCER AGENTS

(75) Inventors: Asish Kumar Banerjee, Kolkata (IN); Venkatachalam Sesha Giri, Kolkata (IN); Rama Mukherjee, Ghaziabad (IN); Kamal K. Kapoor, Ghaziabad (IN); Gautam Desiraju, Hyderabad (IN); Manu Jaggi, Ghaziabad (IN); Anu T. Singh, Ghaziabad (IN); Sankar Kumar Dutta, Kolkata (IN); Kalapatapu V. V. M. Sairam, Hyderabad (IN)

(73) Assignee: Dabur Research Foundation, Ghaziabad (IN)

( * ) Notice: Subject to any disclaimer, the term of this patent is extended or adjusted under 35 U.S.C. 154(b) by 0 days.

(21) Appl. No.: 10/426,026

(22) Filed: Apr. 29, 2003

(65) Prior Publication Data

US 2004/0220197 A1 Nov. 4, 2004

(51) Int. Cl.$^7$ .................... C07C 50/16; C07C 239/28; C07C 263/06; A61K 31/12; A61P 35/00
(52) U.S. Cl. .................... 514/256; 514/374; 514/510; 514/640; 514/680; 514/718; 544/294; 548/215; 560/36; 560/41; 560/326; 564/265; 568/326; 568/329; 568/633
(58) Field of Search ................ 544/294; 548/215; 560/38, 41, 326, 28; 564/265; 568/326, 329, 633; 514/256, 374, 510, 640, 680, 718

(56) References Cited

U.S. PATENT DOCUMENTS 6,372,785 B1   4/2002   Huang .................... 514/532

OTHER PUBLICATIONS

Duffault et al., Synthetic Communications, 28(13), 2467–2481, 1998.*
Morier–Teissier, E., et al. "Synthesis and Antitumor Properties of an Anthraquinone Bisubstituted by the Copper . . . Gly–Gly–L–His" *J. of Medicinal Chemistry*, vol. 36, No. 15, p. 2084–2090, (1993).

Denny, W.A. "DNA–intercalating ligands as anti–cancer drugs: prospects for future design" *Anti–Cancer Drug Design*, vol. 4, p. 241–263, (1989).
Faulds, D., et al. "Mitoxantrone" *Drugs*, vol. 41, No. 3, p. 400–449, (1991).
Luft, B.J. "Mitoxantrone–induced Bradycardia" *Annals of Internal Medicine*, vol. 126, No. 5, p. 409, (1997).
Bailly, J.D., et al. "Natural resistance of acute myeloid leukemia cell lines to mitoxantrone is associated with lack of apoptosis" *Leukemia*, vol. 11, p. 1523–1532, (1997).
Krapcho, A.P, et al. "Synthesis and Antitumor Evaluation of 2,5–Disubstituted–Indazolo[4,3–gh] isoquinolin . . . " *J. of Medicinal Chemistry*, vol. 41, No. 27, p. 5429–5444, (1998).
Lown, J.W., et al. "Characteristics of the Binding of the Anticancer Agents Mitoxantrone and Ametantrone and Related...Acids" *Biochemistry*, vol. 24, p. 4028–4035, (1985).
Zunino, F., et al. "DNA topoisomerase II as the primary target of anti–tumor anthracyclines" *Anti–Cancer Drug Design*, vol. 5, p. 307–317, (1990).
Huang, H–S, et al. "Studies on Anthracenes. 1. Human Telomerase Inhibition and Lipid Peroxidation of 9–Acyloxy . . . Derivatives" *Chem. Pharm. Bull.*, vol. 49, No. 8, p. 969–973, (2001).
Perry, P.J., et al. "Human Telomerase Inhibition by Regioisomeric Disubstituted Amidoanthracene–9, 10–diones" *J. of Medicinal Chemistry*, vol. 41, No. 24, p. 4873–4884, (1998).
Zagotto, G., et al. "New 1,4–anthracene–9,10–dione derivatives as potential anticancer agents" *II Farmaco*, vol. 55, p. 1–5, (2000).
Johnson, R.K., et al. "Experimental Antitumor Activity of Aminoanthraquinones" *Cancer Treatment Reports*, vol. 63, No. 3, p. 425–439, (1979).

* cited by examiner

Primary Examiner—Fiona T. Powers
(74) Attorney, Agent, or Firm—Ladas & Parry LLP

(57) ABSTRACT

The invention relates to the use of novel anthracene based compounds for the inhibition or prevention of the growth or multiplication of cancer cells, and to therapeutic compositions containing such compounds. The invention relates more specifically to the use of hydroanthracene based compounds for the inhibition and/or prevention of cancer of the colon, pancreas, prostate, lung, larynx, ovary, breast, glioblastoma, oral cavity, endothelial cells and leukemias. The agents of the invention form a distinct class, distinct from the anthracene, anthrone or anthraquinone derivatives.

48 Claims, No Drawings

HYDROANTHRACENE BASED COMPOUNDS AS ANTICANCER AGENTS

FIELD OF INVENTION

The invention relates to the use of novel anthracene based compounds for the inhibition or prevention of the growth or multiplication of cancer cells, and to therapeutic compositions containing such compounds. The invention relates more specifically to the use of hydroanthracene based compounds for the inhibition and/or prevention of cancer of the colon, pancreas, prostate, lung, larynx, ovary, breast, glioblastoma, oral cavity, endothelial cells and leukemias. The agents of the invention form a distinct class, distinct from the anthracene, anthrone or anthraquinone derivatives.

BACKGROUND OF THE INVENTION

The discovery of the antitumor activity of 1,4-bis [(aminoalkyl)amino] anthracene-9,10-diones such as ametantrone and mitoxantrone (Zee-Cheng, R. K. V. et al., J. Med. Chem, 21, 291–294, (1978); Zee-Cheng, R. K. V. et al., J. Pharm. Sci., 71, 708–709, (1982); Murdock, K. C. et al., J. Med. Chem., 22, 1024–1030 (1979)) has led to numerous physicochemical and pharmacological studies on the tumoricidal mechanisms of these chemotypes. Krapcho, A. P. et al., J. Med. Chem., 34, 2373–2380, (1991); Morier-Teissier, E. et al., J. Med. Chem., 36, 2084–2090, (1993). A number of studies have indicated that an intercalative interaction with DNA may be a major cellular event. Denny, W. A. Anti-Cancer Drug Design, 4, 241–263 (1989). Mitoxantrone, an anthracene-9,10-dione, has gained an important position in the clinical management of leukemia and lymphomas as well as in combination therapy of advanced breast and ovarian cancers. Faulds, D. et al., Drugs, 41, 400–449 (1991). Although mitoxantrone is endowed with an improved tolerance prolife when compared with doxorubicin and other anthracyclines, significant toxic side effects, notably those associated with myelosuppression and cardiotoxicity, remain. Benekli, M. et al., Ann. Intern. Med., 126, 409 (1997).

Bailly etal. (P. Bailly, J. D. et al., Leukemia, 11, 1523–1532 (1997)) have reported that mitoxantrone shows a cross-resistance to cell histotypes developing resistance against doxorubicin mediated by overexpression of glycoprotein. Several studies suggest that intercalation into DNA is a major cellular event and this intercalative interaction may serve as an anchor for the drug at specific base pair sites, which is then followed by the critical cell-killing events. The biochemical basis for the cardiotoxicity exhibited by mitoxantrone is not fully understood. It is generally believed that the in vivo reduction of the quinone moiety is probably more related to the cardiotoxic side effects of mitoxantrone than to its mechanism of cytotoxicity. Krapcho, A. P., et al., J. Med. Chem., 41, 5429–5444 (1998). The planar tricyclic system is known to intercalate into DNA base pairs and interfere in the transcription and replication processes of the cell. Johnson, R. K. et al., Cancer Treat. Rep., 63, 425–439, (1979); Lown, J. W. et al., Biochemisty, 24, 4028–4035, (1985). The DNA binding affinity (quantified as a binding affinity constant) and the dissociation rate constant for the DNA-ligand complex have been evaluated. Drug-DNA binding constants for ametantrone, mitoxantrone and related congeners with calf thymus DNA show a large sensitivity to the position and number of the OH substitutions and the nature of the charged side chain. Denny, W. A. Anti-Cancer Drug Design, 4, 241–263 (1989).

The compounds based on anthraquinone skeleton occupy a prominent position in cancer chemotherapy, with the naturally occurring aminoglycoside anthracycline doxorubicin and the aminoanthraquinone mitoxantrone both being in clinical use. These and other experimental anthraquinone derivatives are believed to act at the duplex DNA level, probably through the stabilization of a ternary complex with DNA topoisomerase II. Zunino, F. et al., Anti-Cancer Drug Des., 5, 307–317 (1990).

9-Acyloxy-1,8-dichloro-anthracene has been reported to useful in the treatment of allergic, inflammatory and tumour conditions by Hsu-Shan Huang, U.S. Pat. No. 6,372,785 (2002). In addition, the inhibition of lipid peroxidation was detected as was their ability to inhibit the telomere-addition function of the human telomerase enzyme together with their inhibition of the Taq polymerise enzyme Huang Hsu-Shan etal Chem. and Pharmaceutical Bulletin, 49(5), 969–973 (2001).

Additional references disclose 1,4- and 2,6-disubstituted or regioisomeric amidoanthracene-9,10-dione derivatives as inhibitors of human telomerase include Philip J. Perry et al. J. Med. Chem. 41, 3253–3260 (1998) and Philip J. Perry et al. J. Med. Chem. 41, 4873–4884 (1998). Zagotto, G etal. Farmaco, 55(1), 1–5 (2000) have synthesised a new class of D- and L-aminoacyl-9,10-anthraquinone derivatives as potential cytotoxic agents and correlated their activity with the configuration of the chiral aminoacyl moiety.

It is evident from the literature that free radicals and active oxygen species play a key role in both the therapeutic activity and side effects of anthracenone derivatives. The generation of free radicals from quinones occurs by addition of an electron to the quinone to form semi-quinone free radicals which then transfer an electron to molecular oxygen to afford superoxide radical anion. The resulting radical anions ultimately lead to hydroxyl radicals, which can damage cardiac tissue. Despite the attempts to rationalize the cardiotoxicity of anthracene-9,10-dione antitumor agents, few compounds have been shown to possess both good antitumor activity and little or no cardiotoxicity. Consequently there appears to be no way to predict which compounds will be cardiotoxic and which compounds will not. One is thus confronted with the major problem of designing molecules with high efficacy and no toxicity. Krapcho, A. P. et al., J. Med. Chem., 41, 5429–5444 (1998).

The present invention differs from the prior art in the sense that the compounds claimed here are partially reduced anthracenes. Therefore, they have non planar structures and differ from anthracenes, anthraquinones and anthrones, which are planar. This non planarity has therefore different implications for their mechanisms of action and typically, intercalation as it pertains to anthracene based molecules, need not apply.

SUMMARY OF THE INVENTION

The invention provides novel hydroanthracene based compounds selected from a group consisting of compounds represented by the General Formulas (1) to (3).

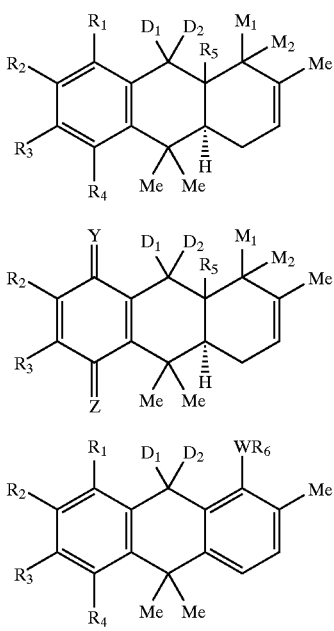

wherein

R₁ to R₄ are the same or different and represent hydrogen, alkyl, hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_1$, $R_2$ or $R_2$, $R_3$ or $R_3$, $R_4$ position, respectively;

$R_5$ is hydrogen, alkyl or alkoxycarbonyl;

$M_1$ is hydrogen, and $M_2$ is $WR_6$ or $M_1$ and $M_2$ together represent X;

W is oxygen or NH;

$R_6$ is hydrogen, alkyl, alkylcarbonyl, tosyl, $COCH(R_7)NHR_8$, $COCH(OR_9)CH(NHR_8)$phenyl, 2,2-Dimethyl-4-phenyloxazolidine-5-carbonyl or 3-substituted-2,2-dimethyl-4-phenyloxazolidine-5-carbonyl, where 3-substitutents may be CO(O-alkyl), CO(O-benzyl) or benzoyl; 2,6-Dioxo-1,2,3,6-tetrahydro-4-carbonyl, or 2,6-disubstituted pyrimidine-4-carbonyl (the substituents may be the same or different and preferably represent chloro, fluoro, amino, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), NH-aryl (preferably, the aryl of NH-aryl is phenyl, 2 or 3 or 4-alkoxyphenyl, 2 or 3 or 4-fluorophenyl, 2 or 3 or 4-bromophenyl, 2,3 or 2,4 or 3,4 or 3,5-dialkoxyphenyl), NH—CH2-aryl (preferably, the aryl of NH-aryl is phenyl, 2 or 3 or 4-alkoxyphenyl, 2 or 3 or 4-fluorophenyl, 2 or 3 or 4-bromophenyl, 2,3 or 2,4 or 3,4 or 3,5-dialkoxyphenyl), 4-morpholino, 1-piperidino or 1-pyrolidino), and their salts, preferred salts are HCl, and HBr salts.

$R_7$ is hydrogen, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl;

$R_8$ is hydrogen, $COCH_3$, $COCF_3$, benzoyl or tert.-butyloxycarbonyl, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl;

$R_9$ is hydrogen, $COCH_3$ or $COCF_3$, benzoyl or tert.-butyloxycarbonyl;

$D_1$ is H and $D_2$ is hydrogen, hydroxy or OAc or $D_1$ and $D_2$ together are carboxy, $NOR_{10}$, or $NR_{11}$;

X, Y and Z are the same or different and represent oxygen, $NOR_{10}$ or $NR_{11}$;

$R_{10}$ is hydrogen or alkyl; and $R_{11}$ is alkyl, benzyl, phenyl, 2 or 3 or 4-alkoxyphenyl, 2 or 3 or 4-fluorophenyl, 2 or 3 or 4-bromophenyl, 2,3 or 2,4 or 3,4 or 3,5-dialkoxyphenyl.

The present invention provides a pharmaceutical composition of novel hydroanthracene based compounds or pharmaceutically acceptable salts of the hydroanthracene based compounds useful for killing or inhibiting multiplication of cancer cells and testing their bio-activity using cultured human cancer cells as the monitor.

DETAILED DESCRIPTION OF THE INVENTION

The present invention is aimed at the development of hydroanthracene based compounds as new anticancer agents.

As described herein, the present invention encompasses compounds selected from a group consisting of compounds represented by the General Formulas (1) to (3)

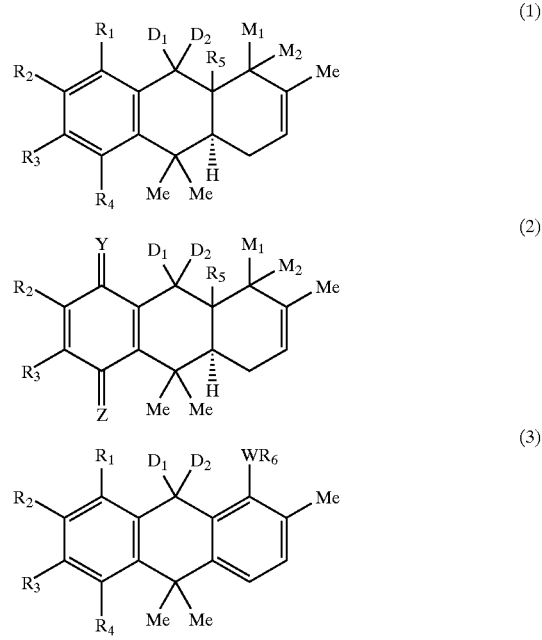

wherein

R₁ to R₄ are the same or different and represent hydrogen, alkyl, hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_1$, $R_2$ or $R_2$, $R_3$ or $R_3$, $R_4$ position, respectively;

$R_5$ is hydrogen, alkyl or alkoxycarbonyl;

$M_1$ is hydrogen, and $M_2$ is $WR_6$ or $M_1$ and $M_2$ together represent X;

W is oxygen or NH;

$R_6$ is hydrogen, alkyl, alkylcarbonyl, tosyl, $COCH(R_7)NHR_8$, $COCH(OR_9)CH(NHR_8)$phenyl, 2,2-Dimethyl-4-phenyloxazolidine-5-carbonyl or 3-substituted-2,2-dimethyl-4-phenyloxazolidine-5-carbonyl, where 3-substitutents may be CO(O-alkyl), CO(O-benzyl) or benzoyl; 2,6-Dioxo-1,2,3,6-tetrahydro-4-carbonyl, or 2,6-disubstituted pyrimidine-4-carbonyl (the substituents may be the same or different and preferably represent chloro, fluoro, amino, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), NH-aryl (preferably, the aryl of NH-aryl is phenyl, 2 or 3 or 4-alkoxyphenyl, 2 or 3 or 4-fluorophenyl, 2 or 3 or 4-bromophenyl, 2,3 or 2,4 or 3,4 or 3,5-dialkoxyphenyl), NH—CH2-aryl (preferably, the aryl of NH-aryl is phenyl, 2 or 3 or 4-alkoxyphenyl, 2 or 3 or 4-fluorophenyl, 2 or 3 or 4-bromophenyl, 2,3 or 2,4 or 3,4 or 3,5-dialkoxyphenyl), 4-morpholino, 1-piperidino or 1-pyrolidino), and their salts, preferred salts are HCl, and HBr salts.

$R_7$ is hydrogen, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl;

$R_8$ is hydrogen, $COCH_3$, $COCF_3$, benzoyl or tert.-butyloxycarbonyl, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl;

$R_9$ is hydrogen, $COCH_3$ or $COCF_3$, benzoyl or tert.-butyloxycarbonyl;

$D_1$ is H and $D_2$ is hydrogen, hydroxy or OAc or $D_1$ and $D_2$ together are carboxy, $NOR_{10}$, or $NR_{11}$;

X, Y and Z are the same or different and represent oxygen, $NOR_{10}$ or $NR_{11}$;

$R_{10}$ is hydrogen or alkyl;

$R_{11}$ is alkyl, benzyl, phenyl, 2 or 3 or 4-alkoxyphenyl, 2 or 3 or 4-fluorophenyl, 2 or 3 or 4-bromophenyl, 2,3 or 2,4 or 3,4 or 3,5-dialkoxyphenyl.

As used herein, alkyl is a group having $C_1$–$C_4$ carbon atoms.

As used herein the term alkoxy refers to O-alkyl groups wherein the alkyl group has 1–4 carbon atoms. The preferred alkyl group is methyl.

As used herein alkylamino and dialkylamino refer to a group wherein one alkyl group or two alkyl groups are bonded to an amino nitrogen, i.e., NH(alkyl) or N(alkyl)$_2$. The NH or N is the bridge connecting the alkyl groups to the tricyclic skeleton of formulae (1) to (3) described in this application. Examples include NHMe, NHEt, or N(Me)$_2$, N(Et)$_2$ and the like.

As used herein, alkylthio refers to an S-alkyl wherein the alkylthio is attached as a substituent through the S atom. The S is the bridge connecting the alkyl group to tricyclic skeleton of formulae (1) to (3) described in this application.

As used herein, alkoxycarbonyl refers to a group of formula Alkyl-O—CO. The carbonyl carbon is connected to the tricyclic skeleton of formulae (1) to (3) described in this application.

Compounds of this invention have linear six-six-six tricyclic ring systems which are tetramethyl-tetrahydroanthracenone, trimethyl-tetrahydro-antracenone, tetramethyl-hexahydro-anthracenol, trimethyl-hexahydro-anthracenol, trimethyl-dihydro-anthracenol, tetramethyl-tetrahydro-anthracenetrione, trimethyl-tetrahydro-anthrcenetrione, hydroxy-tetramethyl-tetrahydro-anthracenedione or hydroxy-trimethyl-hexahydro-anthracenedione derivatives.

To further demonstrate the process for the synthesis of the compounds of General Formulas (1) to (3), the synthetic protocol of their representative compounds depicted below, is given.

Representative Compounds of General Formula (1)
Formulas 4 to 18

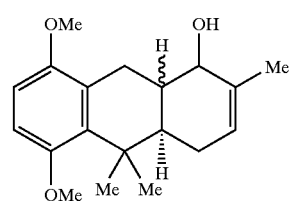

4

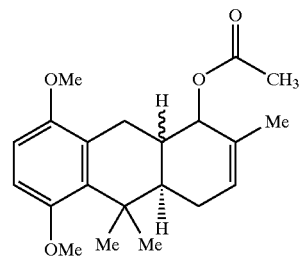

5

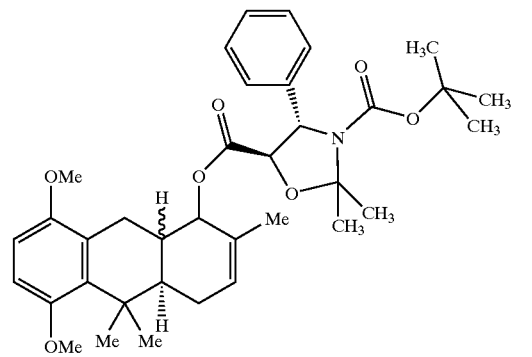

6

7
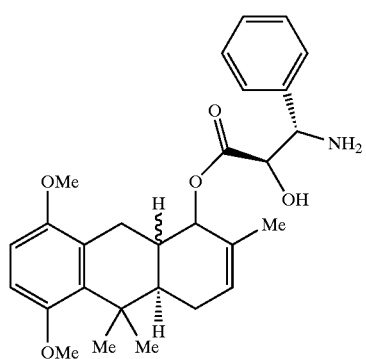
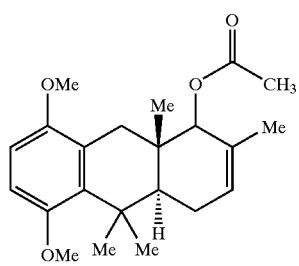
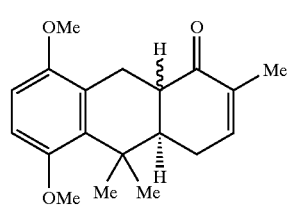
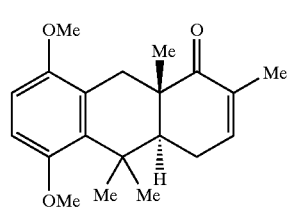
8
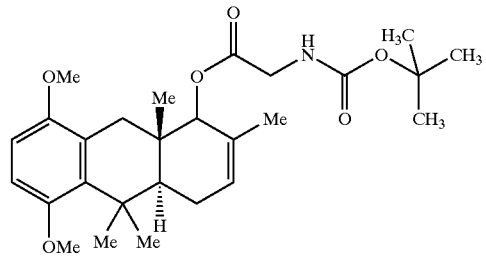
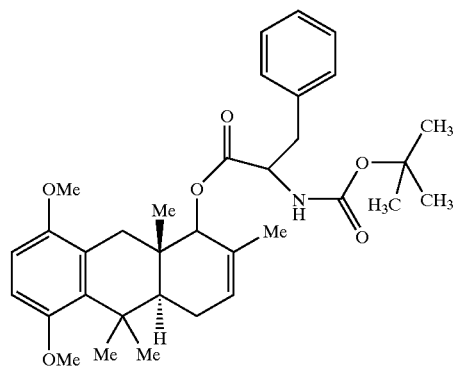
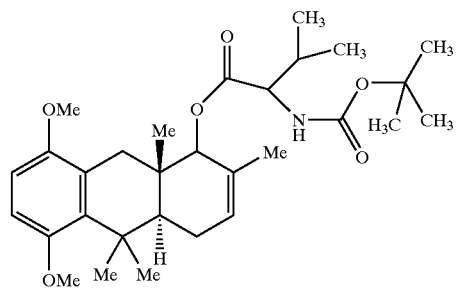
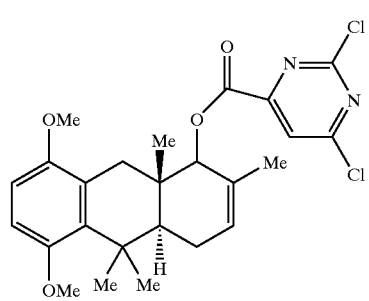

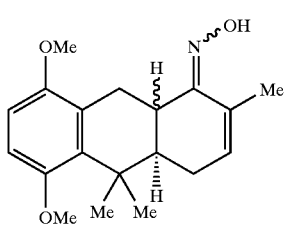
Representative Compounds of General Formula (2)
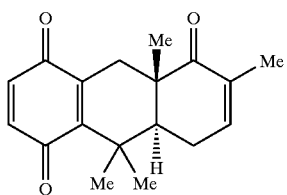
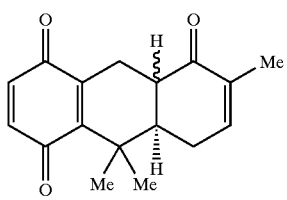
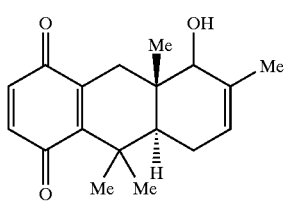
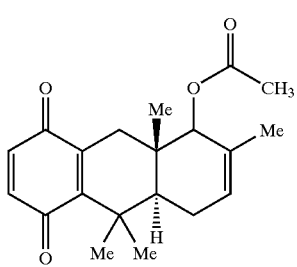
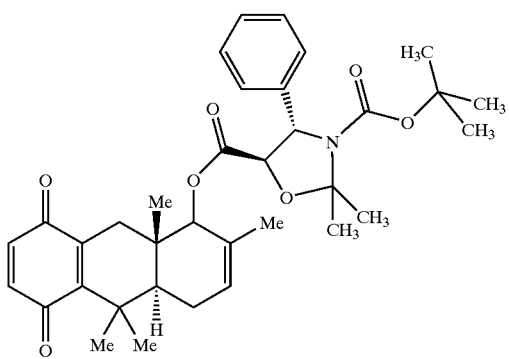
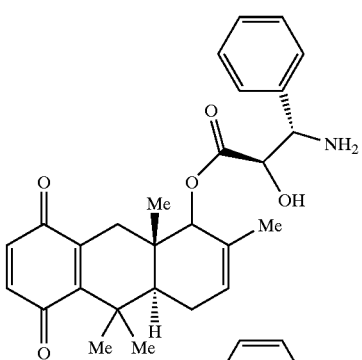
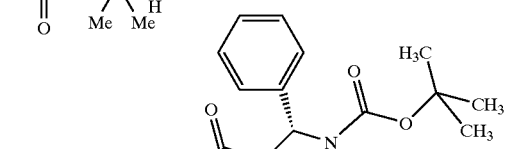
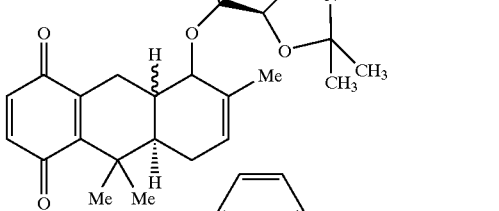
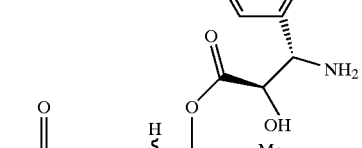
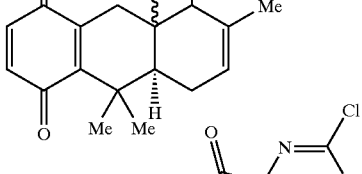
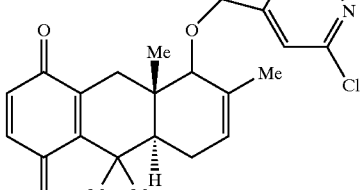
Representative Compounds of General Formula (3)
FIGS. 28 and 29
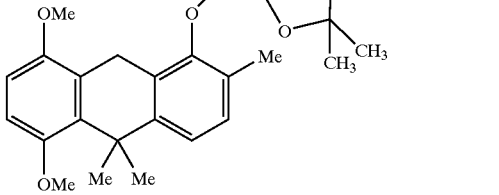

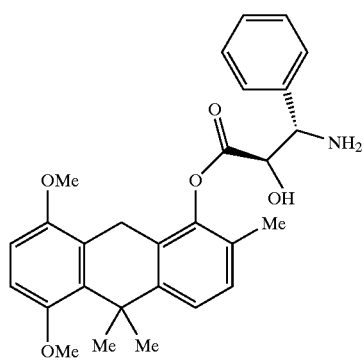

Formula (4) is

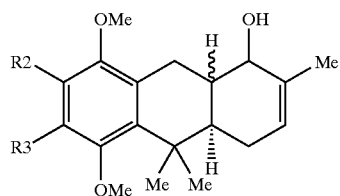

5,8-Dimethoxy-2,10,10,-trimethyl-1,4,4a,9,9a,10-hexahydro-anthracen-1-ol ($R_2=R_3=H$). Derivatives of Formula (4) are compounds where R2, R3 are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (5) is

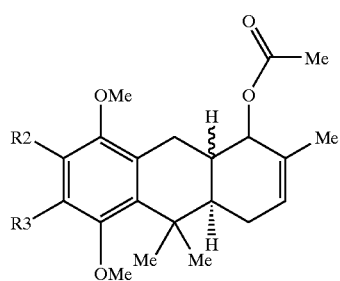

Acetic acid 5,8-dimethoxy-2,10,10-trimethyl-1,4,4a,9,9a,10-hexahydro-anthracene-1-yl ester ($R_2=R_3=H$). Derivatives of Formula (5) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (6) is

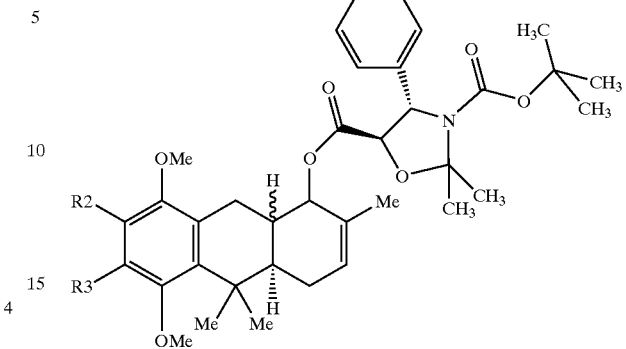

2,2-Dimethyl-4-phenyl-oxazolidine-3,5-dicarboxylic acid 3-tert-butyl ester 5-(5,8-dimethoxy-2,10,10-trimethyl-1,4,4a,9,9a,10-hexahydro-anthrcen-1-yl) ester ($R_2=R_3=H$). Derivatives of Formula (6) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (7) is

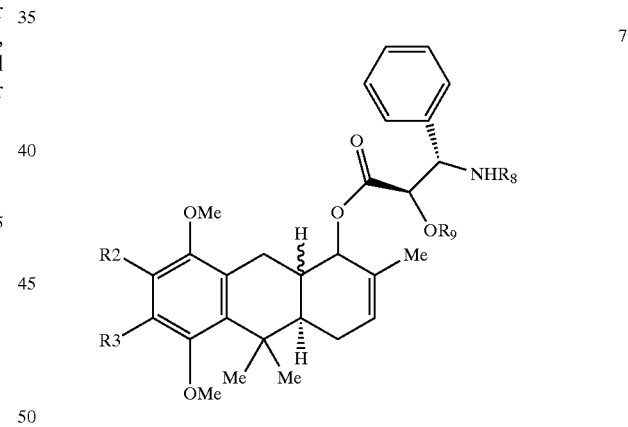

3-Amino-2-hydroxy-3-phenyl-propionic acid 5,8-dimethoxy-2,10,10-trimethyl-1,4,4a,9,9a,10-hexahydro-anthracen-1-yl ester ($R_2=R_3=R_8=R_9=H$). Derivatives of Formula (7) are compounds where $R_2$, $R_3$ are the same or different and represent hydrogen, hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively;

$R_8$ is $COCH_3$, $COCF_3$, benzoyl or tert.-butyloxycarbonyl, alkyl, 4-methylbutyl, benzyl, isopropyl, 1-hydroxyethyl, 2 or 3 or 4-hydroxybenzyl, 2 or 3 or 4-alkoxybenzyl, 3,4- dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl;

$R_9$ is $COCH_3$, $COCF_3$, benzoyl or tert.-butyloxycarbonyl.

Formula (8) is

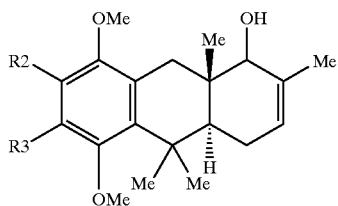

5,8-Dimethoxy-2,9a,10,10-tetramethyl-1,4,4a,9,9a,10-hexahydro-anthracen-1-ol ($R_2$=$R_3$=H). Derivatives of Formula (8) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (9) is

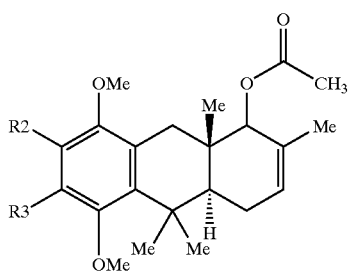

Acetic acid 5,8-dimethoxy-2,9a,10,10-tetramethyl-1,4,4a, 9,9a,10-hexahydro-anthracen-1-yl ester ($R_2$=$R_3$=H). Derivatives of Formula (9) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (10) is

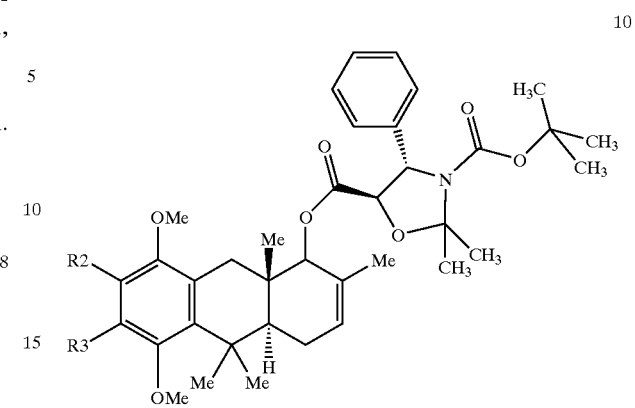

2,2-Dimethyl-4-phenyl-oxazolidine-3,5-dicarboxylic acid 3-tert-butyl ester 5-(5,8-dimethoxy-2,9a,10,10-tetramethyl-1,4,4a,9,9a,10-hexahydro-anthrcen-1-yl) ester ($R_2$=$R_3$=H). Derivatives of Formula (10) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (11) is

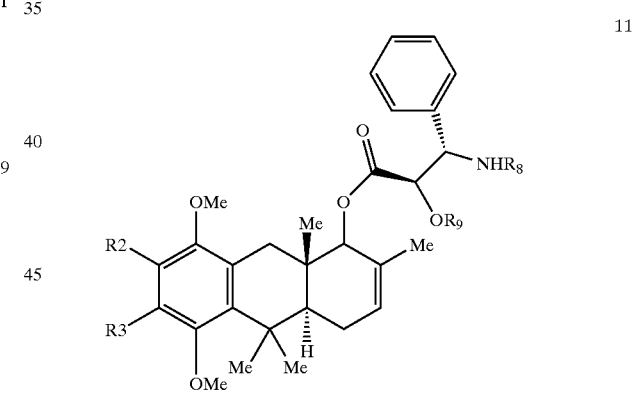

3-Amino-2-hydroxy-3-phenyl-propionic acid 5,8-dimethoxy-2,9a,10,10-tetramethyl-1,4,4a,9,9a,10-hexahydro-anthrcen-1-yl ester ($R_2$=$R_3$=$R_8$=$R_9$=H). Derivatives of Formula (11) are compounds where $R_2$, $R_3$ are the same or different and represent hydrogen, hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively;

$R_8$ is $COCH_3$, $COCF_3$, benzoyl or tert.-butyloxycarbonyl, alkyl, 4-methylbutyl, benzyl, isopropyl, 1-hydroxyethyl, 2 or 3 or 4-hydroxybenzyl, 2 or 3 or 4-alkoxybenzyl, 3,4- dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl;

$R_9$ is $COCH_3$, $COCF_3$, benzoyl or tert.-butyloxycarbonyl.

Formula (12) is

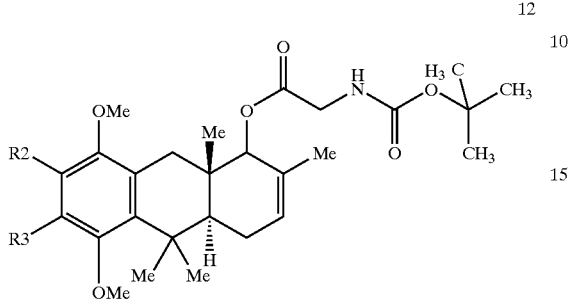

tert-Butoxycarbonylamino-acetic acid 5,8-dimethoxy-2,9a,10,10-tetramethyl-1,4,4a,9,9a10-hexahydro-anthracen-1-yl ester ($R_2$=$R_3$=H). Derivatives of Formula (12) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (13) is

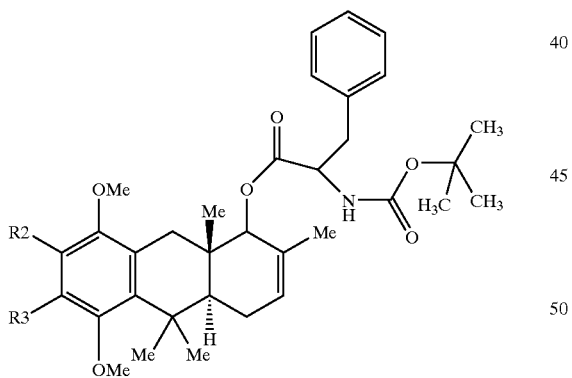

2-tert-Butoxycarbonylamino-3-phenyl-propionic acid 5,8-dimethoxy-2,9a,10,10-tetramethyl-1,4,4a,9,9a,10-hexahydro-anthracen-1-yl ester ($R_2$=$R_3$=H). Derivatives of Formula (13) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (14) is

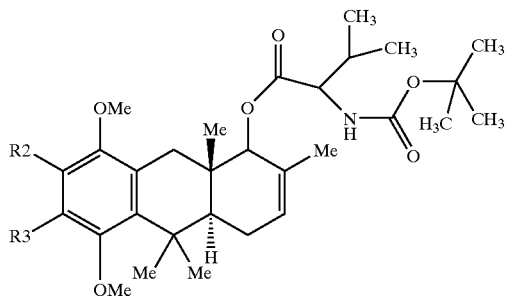

2-tert-Butoxycarbonylamino-3-methyl-butyricacid 5,8-dimethoxy-2,9a,10,10-tetramethyl-1,4,4a,9,9a,10-hexahydr-anthracen-1-yl ester ($R_2$=$R_3$=H). Derivatives of Formula (14) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula 15 is

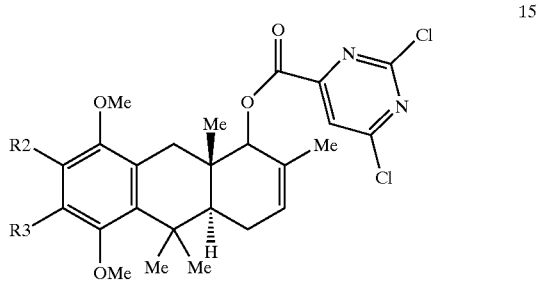

2,6-Dichloro-pyrimidine-4-carboxylicacid-5,8-dimethoxy-2,9a,10,10-tetramethyl-1,4,4a,9,9a,10-hexahydro-anthracen-1-yl ester ($R_2$=$R_3$=H). Derivatives of Formula (15) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (16) is

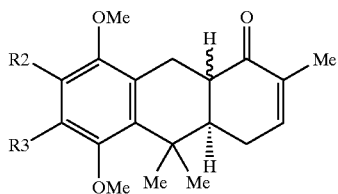

5,8-Dimethoxy-2,10,10-trimethyl-4a,9,9a,10-tetrahydro-4H-anthracen-1-one ($R_2=R_3=H$). Derivatives of Formula (16) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (17) is

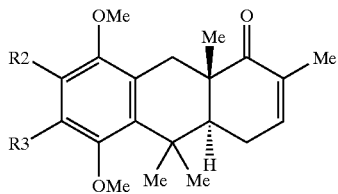

5,8-Dimethoxy-2,9a,10,10-tetramethyl-4a,9,9a,10-tetrahydro-4H-anthracen-1-one ($R_2=R_3=H$). Derivatives of Formula (17) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (18) is

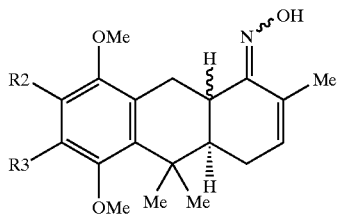

5,8-Dimethoxy-2,10,20,-trimethyl-4a,9,9a,10-tetrahydro-4H-anthracen-1-one oxime ($R2_1=R_3=H$). Derivatives of Formula (18) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (19) is

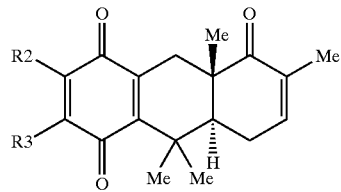

6,9,9,10a-Tetramethyl-8a,9,10,10a-tetrahydro-8H-anthracene-1,4,5-trione ($R_2=R_3=H$). Derivatives of Formula 19 are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (20) is

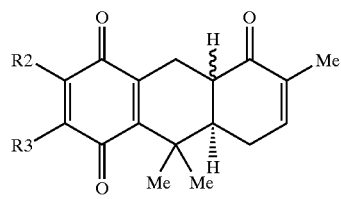

6,9,9-Trimethyl-8a,9, 10,10a-tetrahydro-8H-anthracene-1,4,5-trione ($R_2=R_3=H$). Derivatives of Formula (20) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (21) is

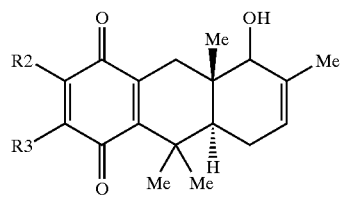

5-Hydroxy-6,9,9,10a-tetramethyl-5,8,8a,9,10,10a-hexahydro-anthracene-1,4-dione trione ($R_2=R_3=H$). Derivatives of Formula 21 are compounds where $R_2$, $R_3$ are the same or different and represent hydroxy, alkoxy, methoxymethyloxy, alkylthio, amino, alkylamino, dialkylamino, alkylcarbonyloxy, NHCOCH₃, NHCOCF₃, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either R₂, R₃ position, respectively.

Formula (22) is

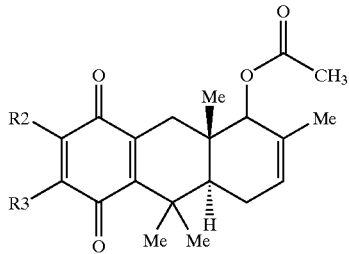

Acetic acid 2,9a,10,10-tetramethyl-5,8-dioxo-1,4,4a,5,8, 9,9a,10-octahydro-anthracen-1-yl ester (R₂=R₃=H). Derivatives of Formula (22) are compounds where R₂, R₃ are the same or different and represent hydroxy, alkoxy, methoxymethyloxy, alkylthio, amino, alkylamino, dialkylamino, alkylcarbonyloxy, NHCOCH₃, NHCOCF₃, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either R₂, R₃ position, respectively.

Formula (23) is

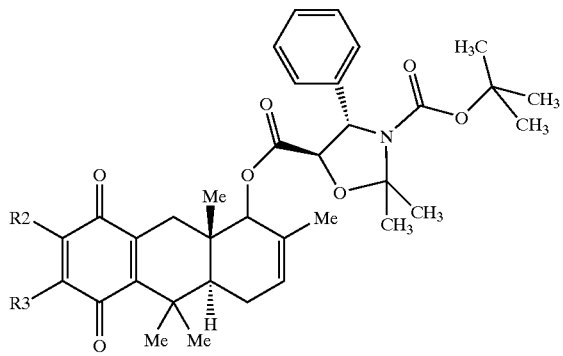

2,2-Dimethyl-4-phenyl-oxazolidine-3,5-dicarboxylic acid 3-tert-butyl ester 5-(2,9a,10,10-tetramethyl-5,8-dioxo-1,4,4a,5,8,9,9a,10-octahydro-anthracen-1-yl) ester (R₂=R₃=H). Derivatives of Formula (23) are compounds where R₂, R₃ are the same or different and represent hydroxy, alkoxy, methoxymethyloxy, alkylthio, amino, alkylamino, dialkylamino, alkylcarbonyloxy, NHCOCH₃, NHCOCF₃, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either R₂, R₃ position, respectively.

Formula (24) is

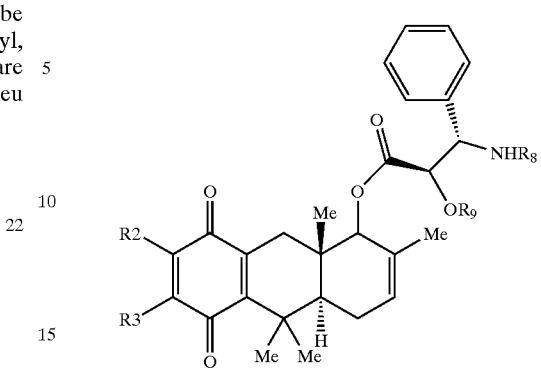

3-Amino-2-hydroxy-3-phenyl-propionic acid 2,9a,10,10-tetramethyl-5,8-dioxo-1,4,4a,5,8,9,9a,10-octahydro-anthracen-1-yl ester (R₂=R₃=R₈=R₉=H). Derivatives of Formula (24) are compounds where R₂, R₃ are the same or different and represent hydroxy, alkoxy, methoxymethyloxy, alkylthio, amino, alkylamino, dialkylamino, alkylcarbonyloxy, NHCOCH₃, NHCOCF₃, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either R₁, R₂ position, respectively;

R₈ is COCH₃, COCF₃, benzoyl or tert.-butyloxycarbonyl, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl; and R₉ is COCH₃, COCF₃, benzoyl or tert.-butyloxycarbonyl.

Formula (25) is

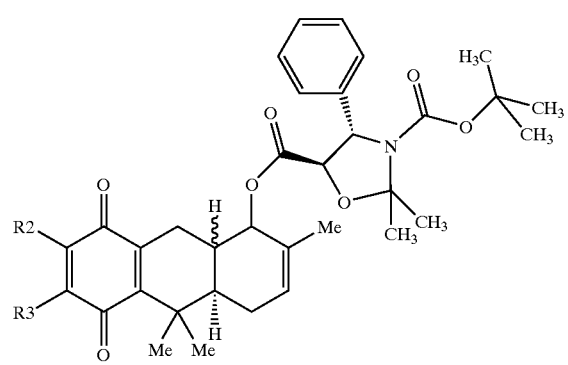

2,2-Dimethyl-4-phenyl-oxazolidine-3,5-dicarboxylic acid 3-tert-butyl ester 5-(2,10,10-trimethyl-5,8-dioxo-1,4,4a,5,8,9,9a,10-octahydro-anthracen-1-yl) ester (R₂=R₃=H). Derivatives of Formula (25) are compounds where R₂, R₃ are the same or different and represent hydroxy, alkoxy, methoxymethyloxy, alkylthio, amino, alkylamino, dialkylamino, alkylcarbonyloxy, NHCOCH₃, NHCOCF₃, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (26) is

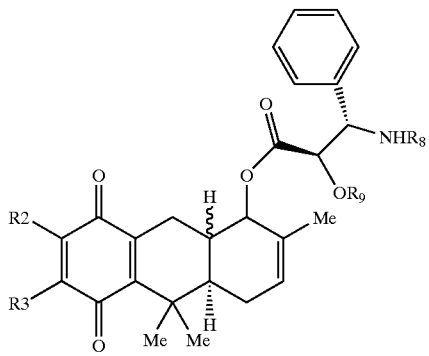

26

3-Amino-2-hydroxy-3-phenyl-propionic acid 2,10,10-trimethyl-5,8-dioxo-1,4,4a,5,8,9,9a,10-octahydro-anthracen-1-yl ester ($R_2=R_3=R_8=R_9=H$). Derivatives of Formula (26) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_1$, $R_2$ position, respectively;

$R_8$ is $COCH_3$, $COCF_3$, benzoyl or tert.-butyloxycarbonyl, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl;

$R_9$ is $COCH_3$, $COCF_3$, benzoyl or tert.-butyloxycarbonyl.

Formula (27) is

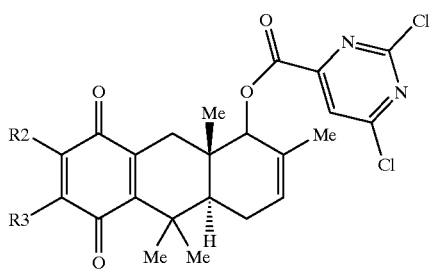

27

2,6-Dichloro-pyrimidine-4-carboxylicacid-2,9a,10,10-tetramethyl-5,8-dioxo-1,4,4a,5,8,9,9a,10-octahydro-anthracen-1-yl ester ($R_2=R_3=H$). Derivatives of Formula (27) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (28) is

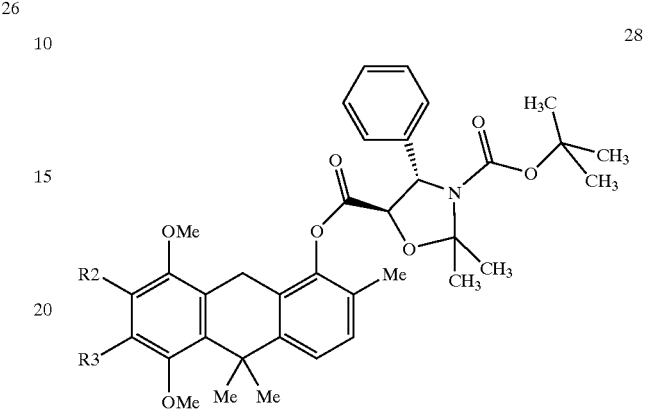

28

2,2-Dimethyl-4-phenyl-oxazolidine-3,5-dicarboxylic acid 3-tert-butyl ester 5-(5,8-dimethoxy-2,10,10-trimethyl-9,10-dihydro-anthracen-1-yl) ester ($R_2=R_3=H$). Derivatives of Formula (28) are compounds where $R_2$, $R_3$ are the same or different and represent hydrogen, hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$ $R_3$ position, respectively.

Formula (29) is

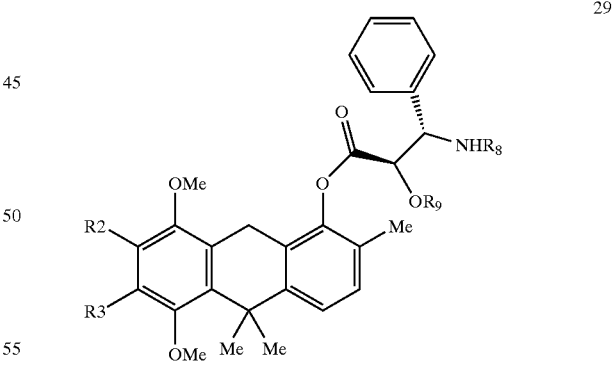

29

3-Amino-2-hydroxy-3-phenyl-propionic acid 5,8-dimethoxy-2,10,10,-trimethyl-9,10-dihydro-anthracen-1-yl ester ($R_2=R_3=R_8=R_9=H$). Derivatives of Formula (29) are compounds s where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively;

$R_8$ is $COCH_3$, $COCF_3$, benzoyl or tert.-butyloxycarbonyl, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl;

$R_9$ is $COCH_3$, $COCF_3$, benzoyl or tert.-butyloxycarbonyl.

Formula (31) is

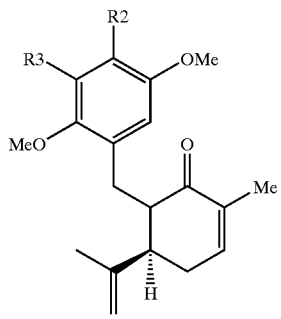

31

6-(2,5-Dimethoxy-benzyl)-5-isopropenyl-2-methyl-cyclohex-2-enone ($R_2=R_3=H$). Derivatives of Formula (31) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (32) is

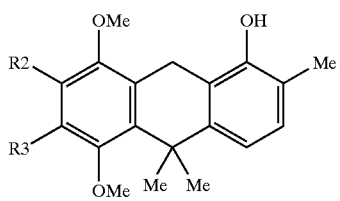

32

5,8-Dimethoxy-2,10,10-trimethyl-9,10-dihydro-anthracen-1-ol ($R_2=R_3=H$). Derivatives of Formula 32 are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

Formula (34) is

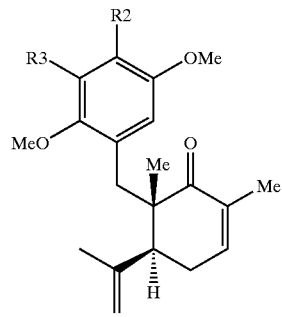

34

6-(2,5-Dimethoxy-benzyl)-5-isopropenyl-2,6-dimethyl-cyclohex-2-enone ($R_2=R_3=H$). Derivatives of Formula (34) are compounds where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent methyl, ethyl, propyl, butyl or t-butyl), and their salts, preferred salts are HCl, and HBr salts, or methylenedioxy group fused in lieu of either $R_2$, $R_3$ position, respectively.

The compounds of formulas (4), (5), (6), (7), (16), (18), (20), (25), (26), (28) and (29) were synthesised from a common intermediate of formula (31), which in turn is derived from the alkylation of (R)-Carvone of formula (30) with 2,5-dimethoxybenzyl bromide. The common intermediate of formula (31) upon carbonation mediated cyclization with $P_2O_5/CH_3SO_3H$ yielded compound of formula (16). $NaBH_4/CeCl_3.7H_2O$ reduction of compound of formula (16) gave compounds of formulas (4). Esterification of compound of formula (4) produced compounds of formulas (5) and (6). The compound of formula (7) is obtained by the acidic hydrolysis of compound of formula (6). Ceric ammonium nitrate (CAN) oxidation of compounds of formulas (6), (7) and (16) afforded the corresponding compounds of formulas (25), (26), (20) and respectively. Pd/Charcoal induced aromatisation of compound of formula (16) furnished compound of formula (32) which was subjected to esterification, without its isolation, with acid (35) to give compound of formula (28) which in turn produced the compound of formula (29) upon acidic hydrolysis. Oximination of compound of formula (16) furnished the compound of formula (18).

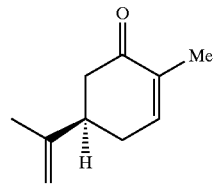

30

31

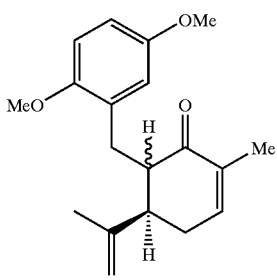

32

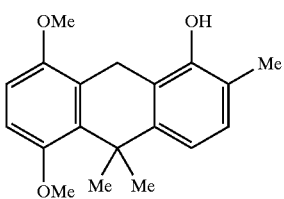

The compounds of formulas (8), (9), (10), (11), (12), (13), (14), (15), (17), (19), (22), (23), (24) and (27) were synthesised from a common intermediate of formula (34), which in turn is derived from the alkylation of 6-methylcarvone of formula (33), prepared by methylation of (R)-carvone of formula (30), with 2,5-dimethoxybenzyl bromide. The common intermediate of formula (34) upon carbonation mediated cyclization with $P_2O_5/CH_3SO_3H$ yielded compound of formula (17). $NaBH_4/CeCl_3.7H_2O$ reduction of compound of formula (17) gave compound of formula (8). Esterification of compound of formula (8) produced compounds of formulas (9), (10), (13), (14) and (15). Ceric ammonium nitrate (CAN) oxidation of compounds of formulas (9), (10), (11), (15) and (17), and afforded the corresponding compounds of formulas (22), (23), (24), (27) and (19) respectively. The compounds of formula (11) were obtained by the acidic hydrolysis of compounds of formula (10).

33

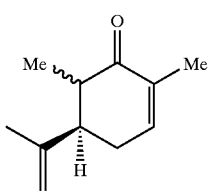

34

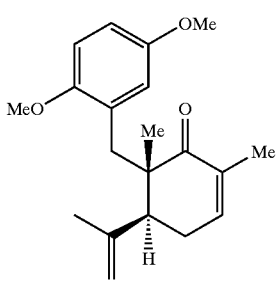

35

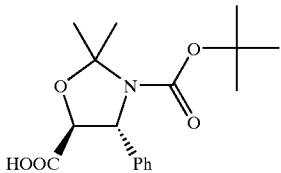

The present invention provides a pharmaceutical composition of novel anthracene based compounds or pharmaceutically acceptable salts of the anthracene based compounds useful for killing or inhibiting multiplication of cancer cells and testing their bio-activity using cultured human cancer cells as the monitor.

In a preferred embodiment, a pharmaceutically acceptable carrier, diluent, or solvent is used. The invention provides a method of treatment for humans, mammals, or other animals suffering from cancer or other tumors. The method may suitably comprise, consist of, or consist essentially of administering a therapeutically effective dose of the pharmaceutical composition so as to kill or inhibit the multiplication of cancer or tumor cells.

The methods of this invention comprise, consist of, or consist essentially of administering systematically to the mammal a therapeutically effective combination of anthracene based compounds. An effective dose of anthracene based compounds or pharmaceutically acceptable salts of the anthracene based compounds ranges from 1 mg/Kg. B. Wt to 300 mg/Kg. B. Wt (preferably 10–100 mg)/Kg. B. Wt) of the mammal, with the dose dependent on the effects sought, the manner of administration, and the cancer being treated. Systemic administration refers to oral, rectal, nasal, transdermal, and parental (i.e., intramuscular, intravenous and subcutaneous). In accordance with good clinical practice, it is preferred to administer the composition at a dose that will produce anticancer effects without causing undue harmful side effects. The composition may be administered either alone or as a mixture with other therapeutic agents such as 5-fluorouracil, methotrexate, etoposide, paclitaxel, taxotere, doxorubicin, daunarubicin, vincristine, vinblastine and other such known and established anticancer drugs.

The compounds of general formulas (1), (2) and (3) and compositions including the compounds of general formulas (1), (2) and (3) can be used for the inhibition and/or prevention of cancer of the colon, pancreas, prostate, lung, larynx, ovary, breast, glioblastoma, oral cavity, endothelial cells and/or leukemias.

The composition may optionally and preferably contain pharmaceutically acceptable diluents, excipients, solvents, binders, stabilizers, and the like. Such diluents may include: RPMI 1649, buffered saline, isotonic NaCl, Ringer's solution, water, distilled water, polyethylene glycol (neat or in water), 2% Tween in water, dimethyl-sulfoxide to 50% in water, propylene glycol (neat or in water), phosphate buffered saline, balanced salt solution, glycerol, and other conventional fluids that are suitable for intravenous administration. Pharmaceutical composition which provide from about 0.1 to 10 gram (preferably 0.5 to 5.0 gram) of the composition per unit dose are preferred and are conventionally prepared as tablets, lozenges, capsules, powders, aqueous or oily suspension, syrups, elixirs, and aqueous solutions. The nature of the pharmaceutical composition employed will, of course, depend on the desired route of administration.

To further assist in the understanding of the present invention and not by way of limitation, the following examples are presented to more clearly describe the present invention.

Abbreviations and General Exptl.

THF=Tetrahydrofuran
LDA=Lithiumdiisopropylamide
DMPU=1,3-Dimethyl-3,4,5,6-tetrahydro-2(1H)-pyrimidone
DMAP=4-Dimethylaminopyridine
DCC=1,3-dicyclohexylcarbodiimide
HOBT=1-Hydroxybenzotriazole hydrate Melting points (m.p.) recorded for the compounds are uncorrected. NMR spectra of $CDCl_3$ solutions were recorded with Bruker DPX-300 spectrometers. In all cases, chemical shifts are in δ (ppm) relative to TMS as internal standard, J-values are given in Hz, and multiplicity is indicated as follows: s, singlet; d, doublet; t, triplet; q, quartet; dd, double doublet; br, broad; m, multiplet. I.R. spectra were recorded using Jasco FT/IR-410. All reagents were of commercial quality and used from freshly opened containers without purifications. Organic solvents were dried by standard methods and distilled before use. Reaction progress was monitored by thin layer chromatography (TLC) on precoated aluminium-backed plates (Merck Kieselgel 60F$_{254}$) and the spots were visualized by UV light. Petroleum spirit used was of boiling range 60–80° C. Ether refers to diethyl ether.

EXAMPLE 1

Preparation of Compound of Formula (31)

To a stirred solution of LDA, prepared from diisopropylamine (3.44 g, 4.76 ml, 34 mmol) and n-BuLi (2.09 g, 16.3 ml of 2 M solution in hexanes, 32 mmol) in THF (30 ml) at −10° C. for 1 h, was added (R)-(−)-carvone (30) (3.78 g, 4 ml, 25 mmol) in dry THF (40 ml) drop-wise over 1 h at the same temperature under nitrogen atmosphere. The stirring was continued for further 2 h. At this temperature was added drop wise a solution of 2,5-dimethoxybenzylbromide (7.52 g, 32.5 mmol) in dry THF (20 ml) during 10 minutes. The reaction mixture was further stirred at −10° C. for 3 h and then the temperature was warmed to room temperature over 1.5 h and stirred for 14 h to complete the reaction (TLC monitored). The reaction mixture was quenched with saturated $NH_4Cl$ solution. The organic layer was separated and THF removed under reduced pressure in rotary evaporator to leave oil. The aqueous part was extracted with ether (200 ml) and the ether layer was combined with the residual oil. The combined ether layer was washed with brine (100 ml) and dried over anhydrous $Na_2SO_4$. After evaporation of the solvent, the residual brown liquid was chromatographed over silica gel (60–120 mesh) (3% ethyl acetate in petroleum ether as eluent) to afford the desired alkylated product (31) (6.4 g, 85%) as light yellow thick liquid.

IR: (neat) 2921, 2832, 1670, 1499, 1461, 1369, 1225, 1049, 895, 802, 710 cm$^{-1}$.

$^1$H NMR (300 MHz in $CDCl_3$): δ 1.64 (3H, s), 1.76 (3H, s), 2.43–2.55 (3H, m), 2.79–2.90 (3H, m), 3.75 (6H, s), 4.71 (1H, s), 4.77 (1H, s), 6.60 (1H, bars), 6.61–6.70 (2H, m), 6.83 (1H, d, J 2.8 Hz).

EXAMPLE 2

Preparation of Compound of Formula (16)

A solution of compound of formula (31) (1 g, 3.3 mmol) in $MeSO_3H$—$P_2O_5$ (10:1) mixture (10 ml) was stirred at 5° C. (ice cold bath) for 1 h 30 minutes to complete the reaction (TLC monitored) under nitrogen atmosphere. The reaction mixture was carefully quenched with crushed ice and extracted with ether (100 ml). Ether layer was washed with $NaHCO_3$, water, brine and dried over anhydrous $Na_2SO_4$. Solvent was evaporated to leave oil. The crude oil was chromatographed over silica gel (60–120 mesh, 3 to 5% EtOAc in petroleum ether as eluent) to afford the cyclized product (16) (856 mg, 85.6%) as a white solid.

m.p.: 120° C.

IR (KBr): v 2938.98, 1665.23, 1593.88, 1469.49, 1365.35, 1255.43, 1058.73, 805.13, 720.28 cm$^{-1}$.

$^1$H NMR ($CDCl_3$, 300 MHz): δ 1.29, 1.35 (3H, s, the two isomers present could be identified in this case in the ratio of 3:1 as seen from the NMR signals), 1.47, 1.50 (3H, s, the two isomers present could be identified in this case in the ratio of 3:1 as seen from the NMR signals), 1.81 (3H, s), 1.94–2.08 (1H, m), 2.28–2.38 (2.5H, m), 2.47–2.55 (1H, m), 2.85–2.91 (0.5H, m), 3.45–3.57 (1H, m), 3.75–3.79 (6H, m), 6.62–6.73 (2H, m), 6.86 (1H, m).

EXAMPLE 3

Preparation of Compounds of Formula (4)

To a stirred suspension of ceric chloride (215 mg, 0.575 mmol) and compound of formula (16) (115 mg, 0.383 mmol) in dry methanol (15 ml) was added at −40° C. under nitrogen atmosphere $NaBH_4$ (51 mg, 1.34 mmol) portion wise. The reaction mixture was stirred for 1 h at −40° C. and then at room temperature for 3 h. Dilute acetic acid was added carefully at 0° C. to destroy excess borohydride. Methanol was removed in a rotary evaporator and the residue dissolved in ether. The ether layer was washed with saturated $NaHCO_3$ solution, water, brine, dried with anhydrous $Na_2SO_4$ and the solvent was evaporated to give the crude product. The crude product was chromatographed over silica gel (60–120 mesh) to give unsaturated alcohol (4) (6% EtOAc in petroleum ether as eluent) as a white solid (95 mg, 82%).

m.p.: 110–112° C. (mixture of stereoisomers).

IR (KBr): v 3404, 2936, 1459, 1437, 1253, 1060 cm$^{-1}$.

$^1$H NMR ($CDCl_3$, 300 MHz, Three major non-separable diastereoisomers): δ 1.19, 1.21 (3H, 2×s), 1.38, 1.41 (3H, 2×s), 1.47, 1.57 (1H, 2×s), 1.78 (3H, bars), 3.76, 3.78 (6H, 2×s), 5.59, 5.45 (1H, 2×bars), 6.61–6.70 (2H, m).

EXAMPLE 4

Preparation of Compound of Formula (5)

To a well-stirred solution of (4) (50 mg, 0.165 mmol) and triethyl amine (84 mg, 115 μl, 0.83 mmol) in dry $CH_2Cl_2$ (3 ml) was added acetic anhydride (42 mg, 39 μl, 0.41 mmol) and DMAP (5 mg) at ice-cold condition under nitrogen atmosphere. The reaction mixture was stirred at room temperature for 2 h. The reaction mixture was quenched with ice and extracted with $CH_2Cl_2$. The organic layer was washed with saturated $NaHCO_3$, brine, dried over anhydrous $Na_2SO_4$ and solvent evaporated. The residue was chromatographed over silica gel (100–200 mesh, 2% ethyl acetate in petroleum ether) to afford (5) (35 mg, 61%) as solid.

m.p.: 121–125° C.

IR (neat): v 3454.85, 2942.84 2835.81, 1736.58, 1593.88, 1459.85, 1436.71, 1367.28, 1334.50, 1251.58, 1172.51, 1060.66 cm$^{-1}$.

$^1$H NMR ($CDCl_3$, 300 MHz): δ 1.37 (3H, s), 1.40 (3H, s), 1.55 (3H, s), 1.73–1.83 (3H, m), 2.01–2.11 (2H, m), 2.14

(3H, s), 2.42–2.53 (1H, m), 2.6–2.71 (2H, m), 3.75 and 3.77 (2×3H, s), 5.52–5.53 (1H, m), 5.64 (1H, brs), 6.62 (1H, d, J 8.8 Hz), 6.68 (1H, d, J 8.8 Hz).

EXAMPLE 5

Preparation of Compound of Formula (6)

To a well-stirred solution of compound of formula (4) (48 mg, 0.16 mmol), compound of formula (35) (77 mg, 0.24 mmol) and DMAP (10 mg) in dry $CH_2Cl_2$ (1 ml) was added DCC (54 mg, 0.24 mmol) at 0° C. under nitrogen atmosphere. The reaction mixture was warmed to room temperature and stirred for 12 h to complete the reaction (TLC monitored). Solvent was removed in a rotary evaporator and the residue left was chromatographed over silica gel (100–200 mesh, 10% EtOAc in petroleum ether as eluent) to afford the desired ester (6) (114 mg, 97%) as a white foamy solid.

m.p.: 73–75° C.

IR (KBr): ν 2973.70, 2936.09, 2834.85, 1750.08, 1702.84, 1595.81, 1457.92, 1372.10, 1253.50, 1176.36 $cm^{-1}$.

$^1$H NMR(CDCl$_3$, 300 MHz): δ 1.16–1.25 (10H, bs), 1.30–1.41 (5H, m), 1.48 (2H, s), 1.62 (2H, s), 1.70–1.81 (9H, m), 2.02–2.24 (2H, m), 2.48–2.73 (2H, m), 3.13, 3.19 (1H, dd, J 5.5, 18.3 Hz), 3.72–3.80 (6H, several s), 4.57 (1H, d, J 5.4 Hz), 5.08–5.23 (1H, bs), 5.52 (1H, bars), 5.69–5.73 (1H, m), 6.60–6.71 (2H, m), 7.29–7.40 (5H, m).

EXAMPLE 6

Preparation of Compound of Formula (20)

To a stirred solution of compound of formula (16) (50 mg, 0.17 mmol) in acetonitrile-water mixture (3 ml, $CH_3CN:H_2O::2:1$) under nitrogen atmosphere at 0° C., a solution of ceric ammonium nitrate (275 mg, 0.5 mmol) in acetonitrile-water mixture (4 ml, $CH_3CN:H_2O::2:1$) was added drop-wise. It was stirred for 20 minutes at 0° C. (till completion of the reaction, TLC monitored). The solvent was removed in rotary evaporator and the residue dissolved in ethyl acetate. The ethyl acetate layer was washed with water, brine, dried with anhydrous $Na_2SO_4$ and the solvent evaporated to give the crude product as an yellow oil. Purification of the oil over silica gel (60–120 mesh, 6–8% EtOAc in petroleum ether) afforded the pure compound (20) (36 mg, 80%) as yellow solid.

m.p.: 125–140° C. (Stereoisomeric mixture)

IR (KBr): ν 2926.45, 1652.70, 1595.81, 1455.49, 1385.60, 1293.04, 1097.30, 1044.26, 960.38, 841.78, 443.55 $cm^{-1}$.

$^1$H NMR (CDCl$_3$, 300 MHz): δ 1.27 (3H, s), 1.37–1.40 (7H, m), 1.61 (3H, s), 1.80–1.94 (6H, m), 2.02–2.10 (2H, bs), 2.22–2.52 (6H, m), 2.69–2.86 (1H, m), 3.20–3.28 (1H, m), 6.60–6.70 (3H, m), 6.85 (1H, d, J 5.29 Hz).

EXAMPLE 7

Preparation of Compound of Formula (25)

To a stirred solution of (6) (55 mg, 0.09 mmol) in acetonitrile-water mixture (3 ml, $CH_3CN:H_2O::2:1$) under nitrogen atmosphere at 0° C., a solution of ceric ammonium nitrate (138 mg, 0.25 mmol) in acetonitrile-water mixture (3 ml, $CH_3CN:H_2O::2:1$) was added drop-wise. It was stirred for 30 minutes at 0° C. (till completion of the reaction, TLC monitored). The solvent was removed in rotary evaporator and the residue dissolved in ethyl acetate. The ethyl acetate layer was washed with water, brine, dried with anhydrous $Na_2SO_4$ and the solvent evaporated to give the crude product as yellow oil. Purification of the oil over silica gel (60–120 mesh, 10% EtOAc in petroleum ether) afforded the pure quinone (25) (45 mg, 87%) as a foamy yellow solid.

m.p.: 70–72° C.

IR (KBr): ν 3449.06, 2975.62, 2930.31, 1750.08, 1702.84, 1654.62, 1455.03, 1372.10, 1290.14, 1254.47 $cm^{-1}$.

$^1$H NMR (CDCl$_3$, 300 MHz): δ 1.14–1.43 (18H, m), 1.64–1.79 (9H, m), 2.03–2.32 (3H, m), 2.86, 2.93 (1H, dd, J 5.7, 5.3 Hz), 4.52–4.57 (1H, m), 5.05–5.18 (1H, bars), 5.43–5.47 (1H, m), 5.66 (1H, bars), 6.60, 6.65 (2H, 2d, J 9.5, 9.7 Hz), 7.30–7.36 (5H, m).

EXAMPLE 8

Preparation of Compound of Formula (26)

To a stirred solution of compound of formula (7) (20 mg, 0.039 mmol) in acetonitrile-water mixture (2 ml, $CH_3CN:H_2O::2:1$) under nitrogen atmosphere at 0° C., a solution of ceric ammonium nitrate (66 mg, 0.12 mmol) in acetonitrile-water mixture (3 ml, $CH_3CN:H_2O::2:1$) was added drop-wise. It was stirred for 30 minutes at 0° C. (till completion of the reaction, TLC monitored). The solvent was removed in rotary evaporator and the residue dissolved in ethyl acetate. The ethyl acetate layer was washed with water, brine, dried with anhydrous $Na_2SO_4$ and the solvent evaporated to give the crude product as yellow oil. Purification of the oil over silica gel (100–200 mesh, 70% EtOAc in petroleum ether) afforded the pure quinone (26) (15 mg, 80%) as a yellow solid.

m.p.: 154–155° C.

IR (KBr): ν 3350.71, 3063.37, 2924.52, 1738.51, 1652.70, 1529.27, 1452.14, 1373.07, 1294.00, 1209.15, 1098.26 $cm^{-1}$.

$^1$H NMR (CDCl$_3$, 300 MHz): δ 1.27–1.39 (7 H, m), 1.62–1.71 (3H, m), 1.88–2.20 (5H, m), 2.27–2.37 (1H, m), 2.46–2.52 (0.5H, m), 2.60, 2.67 (0.5H, 2d, J 5.12 & 4.66 Hz), 4.21–4.32 (1H, m), 4.50 (0.5H, d, J 1.5 Hz), 4.59 (0.5H, d, J 2.1 Hz), 5.51–5.64 (2H, m), 6.22–6.39 (1H, m), 6.57–6.71 (2H, m), 7.28–7.53 (5H, m)

EXAMPLE 9

Preparation of Compound of Formula (28)

To a well-stirred solution of compound of formula (16) (100 mg, 0.33 mmol) in dry xylene (15 ml) was added Pd-charcoal (10%, 150 mg) and the reaction mixture was heated at 222° C. under $N_2$ atmosphere using an oil bath for 3 h. The reaction mixture was cooled and filtered through celite and the celite pad was washed with dry EtOAc (20 ml). Solvent was removed under reduced pressure using rotary evaporator to leave the aromatic product (32) as greenish oil (85 mg), which was directly used in the next step.

To a well-stirred solution of (32) (85 mg, 0.28 mmol), (35) (128 mg, 0.4 mmol) and DMAP (10 mg) in dry $CH_2Cl_2$ (1 ml) was added DCC (82 mg, 0.4 mmol) at 0° C. under $N_2$ atmosphere. The reaction mixture was warmed to room temperature and stirred for 12 h to complete the reaction (TLC monitored). Solvent was removed in a rotary evaporator and the residue left was chromatographed over silica gel (100–200 mesh, 8% EtOAc in petroleum ether as eluent)

to afford the desired ester (28) (135 mg, 67% in two steps) as a yellow foamy solid.

m.p.: 84–85° C.

IR (KBr): ν 2976.59, 1774.19, 1702.84, 1600.63, 1458.89, 1372.10, 1256.40, 1168.65, 1077.05, 702.93 cm$^{-1}$.

$^1$H NMR (CDCl$_3$, 300 MHz): δ 1.21 (9H, bars), 1.47 (3H, s), 1.76 (3H, s), 1.85 (3H, s), 1.89 (3H, s), 2.14 (5H, s), 3.71 (3H, s), 3.85 (3H, s), 4.86 (1H, d, J 5.4 Hz), 5.42 (1H, bars), 6.71 (1H, d, J 8.7 Hz), 6.80 (1H, d, J 8.7 Hz), 7.14 (1H, d, J 8.0 Hz), 7.30–7.38 (5H, m), 7.48 (1H, d, J 8.0 Hz).

EXAMPLE 10

Preparation of Compound of Formula (29)

To a well-stirred solution of compound of formula (28) (75 mg, 0.124 mmol) in ethyl acetate (5 ml) under nitrogen atmosphere, HCl (3 ml, 4N solution) was added drop-wise at room temperature. The reaction mixture was then stirred at room temperature for 4 days (TLC monitored). Ammonia solution (7%) was then added drop-wise at 5° C. (ice cold condition) till the resulting solution was neutral and the resulting mixture was extracted with ethyl acetate. The ethyl acetate layer was washed with water, brine, dried over anhydrous Na$_2$SO$_4$ and the solvent removed under reduced pressure in a rotary evaporator to get the crude solid. The residue was chromatographed over silica gel (100–200 mesh, 50% ethyl acetate in petroleum ether) to afford the pure amino alcohol (29) (38 mg, 67%) as a yellow solid.

m.p.: 72–74° C.

IR (KBr): ν 3340.10, 2935.13, 1755.87, 1600.63, 1460.81, 1256.40, 1155.15, 1071.26, 800.31, 705.82, 546.72 cm$^{-1}$.

$^1$H NMR (CDCl$_3$, 300 MHz): δ 1.62 (1H, d, J 9.2 Hz), 1.76 (6H, s), 1.97–2.26 (5H, m), 3.76–3.80 (5H, m), 3.84 (3H, s), 4.81 (2H, bars), 6.68, 6.78 (2H, 2d, J 8.88 Hz), 7.12 (1H, d, J 8.17 Hz), 7.28–7.41 (4H, m), 7.59 (2H, d, J 7.23 Hz).

EXAMPLE 11

Preparation of Compound of Formula (18)

To a well stirred solution of compound of formula (16) 50 mg, 0.166 mmol) in dry EtOH (5 ml) was added sodium acetate (20.5 mg, 0.25 mmol) and hydroxyl amine hydrochloride (18 mg, 0.25 mmol). The reaction mixture was refluxed for 4 h 30 minutes under nitrogen atmosphere to complete the reaction (TLC monitored). Ethanol was evaporated under reduced pressure in a rotary evaporator and the residue was taken in ethyl acetate. The ethyl acetate layer was washed with water, brine, dried over anhydrous Na$_2$SO$_4$ and the solvent was evaporated under reduced pressure in a rotary evaporator to leave the crude solid. The crude solid was chromatographed over silica gel (60–120 mesh, 10 EtOAc in petroleum ether) to afford the oxime (18) (37 mg, 70%) as white solid.

m.p.: 233–235° C.

IR (KBr): ν 3276, 2937, 1457, 1435, 1254, 1084, 1062, 955 cm$^{-1}$ $^1$H NMR (CDCl$_3$, 300 MHz): δ 1.43 (3H, s), 1.46 (3H, s), 1.71–1.75 (1H, m), 1.85 (3H, s), 1.96–2.06 (1H, m), 2.21–2.40(2H, m), 2.97 (1H, dd, J 6, 18 Hz), 3.75 (3H, s), 3.77 (3h, s), 3.92–3.96 (1H, m), 5.99 (1H, m), 6.62 (1H, d, J 8 Hz), 6.70 (1H, d, J 8 Hz), 7.97 (1H, bars).

EXAMPLE 12

Preparation of Compound of Formula (33)

To a stirred solution of diisopropylamine (11.7 g, 16.2 ml, 116 mmol) in dry THF (120 ml), was added n-BuLi (60 ml of 1.6 M solution in hexanes, 120 mmol) drop-wise at −10° C. over 1 h 40 minutes, under nitrogen atmosphere. The resulting yellowish solution was stirred for an additional 30 minutes at the same temperature; this was followed by drop-wise addition of a solution of (R)-(−)-carvone (30) (16.3 ml, 15.63 g, 104 mmol) in dry THF (80 ml) over 2 h at the same temperature. After stirring for another 30 minutes, CH$_3$I (32.6 ml, 74.33 g, 523 mmol) was added rapidly to the reaction mixture and the stirring was continued for further 2 h. The reaction mixture was quenched with a saturated solution of NH$_4$Cl and organic phase was separated. From the organic part THF was removed in a rotary evaporator to leave oil. The aqueous part was extracted with hexane (3×150 ml) and combined with the oil. The combined organic extract was washed with HCl (5%, 200 ml), water (200 ml), Na$_2$S$_2$O$_3$ (5%, 200 ml), water (200 ml), brine (200 ml), dried over anhydrous Na$_2$SO$_4$. After evaporation of the solvent, the residual yellowish oil on short path distillation afforded the desired product (33) (15.56 g, 91%) as colourless oil.

b.p. 120–122° C./10 mm Hg.

IR (neat) 2975, 2930, 1668, 1449, 1375, 890 cm$^{-1}$.

$^1$H NMR (300 MHz in CDCl$_3$):(mixture of two diastereoisomers epimeric at C-6) δ 0.92 and 1.04 (d, J 6 and 7 Hz, 3H in a ratio of ea 1:1) 1.78 and 1.73 br s, 6H), 2.1–2.85 (m, 8H), 4.82 (m, 2H), 6.70 (m, 1H).

EXAMPLE 13

Preparation of Compound of Formula (34)

To a stirred solution of LDA, prepared from diisopropylamine (285 g, 4 ml, 30 mmol) and n-BuLi (1.73 g, 17 ml of 1.6 M solution in hexanes, 27 mmol) in THF (100 ml) at −20° C. for 1 h, was added methyl carvone (33) (4 g, 24 mmol) in dry THF (20 ml) drop-wise over 35 minutes at the same temperature under nitrogen atmosphere. The stirring was continued for further 2 h. The temperature of the reaction mixture was lowered to −78° C. and at this temperature was added at once a solution of 2,5-dimethoxybenzyl bromide (5.95 g, 26.9 mmol) and DMPU (3.18 g, 3 ml, 25 mmol) in dry THF (20 ml). The reaction mixture was further stirred at −78° C. for 2 h and then the temperature was warmed to 0° C. over 1.5 h and stirred for 45 minutes to complete the reaction (TLC monitored). The reaction mixture was quenched with saturated NH$_4$Cl solution. The organic layer was separated and THF removed under reduced pressure in rotary evaporator to leave oil. The aqueous part was extracted with ether (200 ml) and the ether layer was combined with the residual oil. The combined ether layer was washed with brine (100 ml) and dried over anhydrous Na$_2$SO$_4$. After evaporation of the solvent, the residual brown liquid was chromatographed over silica gel (60–120 mesh) (3% ethyl acetate in petroleum ether as eluent) to afford the desired alkylated product (34) (7 g, 90%) as solid.

m.p.: 52–55° C.

IR (neat): 2955, 2910, 2834, 1665, 1500, 1444, 1221, 1051, 1024, 900 cm$^{-1}$.

$^1$H NMR (300 MHz in CDCl$_3$): δ 0.94 (3H, s), 1.52 (3H, s), 1.83 (3H, s), 2.09–2.26 (1H, m), 2.73 (1H, d, J 6.5 Hz), 2.84 (1H, d, J 13.2 Hz), 2.99 (1H, d, J 13.3 Hz), 3.01–3.11 (1H, m), 3.71 (3H, s), 3.74 (3H, s), 4.61 (1H, s), 4.65 (1H, s).

EXAMPLE 14

Preparation of Compound of Formula (17)

A solution of (34) (1 g, 3.18 mmol) in MeSO$_3$H—P$_2$O$_5$ (10:1) mixture (10 ml) was stirred at 5° C. (ice cold bath) for 1 h 30 minutes to complete the reaction (TLC monitored) under $N_2$ atmosphere. The reaction mixture was carefully quenched with crushed ice and extracted with ether (100 ml). Ether layer was washed with $NaHCO_3$, water, brine and dried over anhydrous $Na_2SO_4$. Solvent was evaporated to leave oil. The crude oil was chromatographed over silica gel (60–120 mesh, 3 to 5% EtOAc in petroleum ether as eluent) to afford the cyclised product (17) (800 mg, 80%) as a white solid.

m.p. 88–90° C.

IR (KBr): ν 3430.74, 2954.41, 1663.30, 1594.84, 1457.92, 1366.32, 1330.64, 1253.50, 1071.26, 963.27 $cm^{-1}$.

$^1$H NMR ($CDCl_3$, 300 MHz): δ 1.01 (3H, s), 1.43 (3H, s), 1.45 (3H, s), 1.81 (3H, br s), 2.09 (1H, dd, J 11.4, 4.5 Hz), 2.34 (1H, d, J 17.5 Hz), 2.45–2.54 (2H, m), 3.43 (1H, d, J 17.6 Hz), 3.78 (3H, s), 3.79 (3H, s), 6.66, 6.75 (2H, 2d, J 8.9 Hz), 6.85–6.87 (1H, m).

EXAMPLE 15

Preparation of Compound of Formula (8)

To a suspension of ceric chloride (2.57 g, 6.9 mmol) in dry methanol (50 ml), a solution of (17) (1.445 g, 4.6 mmol) in dry methanol (10 ml) was added at −40° C. under $N_2$ atmosphere. To this stirred solution was added $NaBH_4$ (392 mg, 10.35 mmol) portion wise. The reaction mixture was stirred for 1 h at −40° C. and then at room temperature for 24 h. Dilute acetic acid was added carefully at 0° C. to destroy excess borohydride. Methanol was removed in a rotary evaporator and the residue dissolved in ether. The ether layer was washed with saturated $NaHCO_3$ solution, water, brine, dried with anhydrous $Na_2SO_4$ and the solvent was evaporated to give the crude product. The crude product was chromatographed over silica gel (100–200 mesh, 10% EtOAc in petroleum ether as eluent) to give alcohol (8) (1.425 g, 98%) as white solid.

m.p.: 117–119° C.

IR (KBr): ν 3550.31, 2955.38, 2911.02, 2833.88, 2025.85, 1813.72, 1592.91, 1456.96, 1436.71, 1379.82, 1360.53, 1334.50, 1252.54, 1197.58, 1172.51, 1132.97, 1058.73 $cm^{-1}$.

$^1$H NMR ($CDCl_3$, 300 MHz): δ 0.85 (3H, s), 1.38 (3H, s), 1.41 (3H, s), 1.75–1.80 (4H, m), 2.06–2.24 (3H, m), 3.34 (1H, d, J 16.9 Hz), 3.77 (3H, s), 3.79 (3H, s), 3.92 (1H, br s), 5.54 (1H, br s), 6.67 (1H, d, J 8.8 Hz), 6.73 (1H, d, J 8.8 Hz).

EXAMPLE 16

Preparation of Compound of Formula (9)

To a well-stirred solution of (8) (50 mg, 0.158 mmol) and triethyl amine (80 mg, 110 μl, 0.791 mmol) in dry $CH_2Cl_2$ (1 ml) was added acetic anhydride (40 mg, 38 μl, 0.395 mmol) and DMAP (5 mg) at ice-cold condition under nitrogen atmosphere. The reaction mixture was stirred at room temperature for 2 h. The reaction mixture was quenched with ice and extracted with $CH_2Cl_2$. The organic layer was washed with saturated $NaHCO_3$, brine, dried over anhydrous $Na_2SO_4$ and solvent evaporated. The residue was chromatographed over silica gel (60–120 mesh, 5–6% ethyl acetate in petroleum ether) to afford (9) (49 mg, 87%) as colorless oil.

IR (neat): ν 3454.85, 2942.84 2835.81, 1736.58, 1593.88, 1459.85, 1436.71, 1367.28, 1334.50, 1251.58, 1172.51, 1060.66 $cm^{-1}$.

$^1$H NMR ($CDCl_3$, 300 MHz): δ 0.90 (3H, s), 1.38 (3H, s), 1.41 (3H, s), 1.55 (3H, s), 1.88 (1H, dd, J 5.4 & 11.2 Hz), 2.12–2.33 (3H, m, overlapped by 3H, s at δ 2.19), 3.03 (1H, d, J 16.9 Hz), 3.74 (3H, s), 3.79 (3H, s), 5.40 (1H, s), 5.59 (1H, s), 6.65 (1H, d, J 8.8 Hz), 6.71 (1H, d, J 8.8 Hz).

EXAMPLE 17

Preparation of Compound of Formula (10)

To a well-stirred solution of (8) (60 mg, 0.189 mmol), protected acid (35) (85 mg, 0.265 mmol) and DMAP (10 mg) in dry $CH_2Cl_2$ (1 ml) was added DCC (45 mg, 0.208 mmol) at 0° C. under nitrogen atmosphere. The reaction mixture was warmed to room temperature and stirred for 5 h to complete the reaction (TLC monitored). Solvent was removed in a rotary evaporator and the residue left was chromatographed over silica gel (100–200 mesh, 5–6% EtOAc in petroleum ether as eluent) to afford the desired ester (10) (114 mg, 97%) as a white foamy solid.

m.p.: 73–74° C.

IR (KBr): ν 3453.88, 2977.55, 2937.06, 2835.81, 1737.55, 1702.84, 1594.84, 1457.92, 1378.85, 1253.50 $cm^{-1}$.

$^1$H NMR ($CDCl_3$, 300 MHz): δ 0.87 (3H, s), 1.19 (9H, br s), 1.38 (3H, s), 1.42 (3H, s), 1.62 (3H, s), 1.77 (3H, s), 1.82 (3H, s), 1.86–1.92 (1H, m), 2.17 (2H, d, J 16.9 Hz), 2.24–2.28 (1H, m), 3.05 (1H, d, J 17.2 Hz), 3.72 (3H, s), 3.78 (3H, s), 4.63 (1H, d, J 4.8 Hz), 5.26–5.29 (1H, br s), 5.52 (1H, br s), 5.64 (1H, br s), 6.63, 6.71 (2H, 2d, J 8.8 Hz), 7.36 (5H, m).

EXAMPLE 18

Preparation of Compound of Formula (22)

To a stirred solution of (9) (35 mg, 0.097 mmol) in acetonitrile-water mixture (1 ml, $CH_3CN:H_2O::2:1$) under nitrogen atmosphere at 0° C., a solution of ceric ammonium nitrate (160 mg, 0.293 mmol) in acetonitrile-water mixture (3 ml, $CH_3CN:H_2O::2:1$) was added drop-wise. It was stirred for 20 minutes at 0° C. (till completion of the reaction, TLC monitored). The solvent was removed in rotary evaporator and the residue dissolved in ethyl acetate. The ethyl acetate layer was washed with water, brine, dried with anhydrous $Na_2SO_4$ and the solvent evaporated to give the crude product as yellow oil. Purification of the oil over silica gel (60–120 mesh, 9% EtOAc in petroleum ether) afforded the pure quinone (22) (27 mg, 85%) as a yellow solid.

m.p.: 153–155° C.

IR (KBr): ν 3452.92, 2978.52, 2916.81, 1737.55, 1649.80, 1602.56, 1435.74, 1364.39, 1293.04, 1236.15, 1121.40, 1095.37 $cm^{-1}$.

$^1$H NMR ($CDCl_3$, 300 MHz): δ 0.90 (3H, s), 1.32 (3H, s), 1.35 (3H, s), 1.57 (3H, s), 1.76 (1H, dd, J 5.8 & 10.9 Hz), 1.99 (1H, d, J 19.3 Hz), 2.06–2.32 (2H, m, overlapped by a 3H, s at δ 2.19), 2.78 (1H, d, J 19.3 Hz), 5.36 (1H, s), 5.57 (1H, s), 6.61 (1H, d, J 9.9 Hz), 6.69 (1H, d, J 10.0 Hz)

EXAMPLE 19

Preparation of Compound of Formula (19)

To a stirred solution of (17) (100 mg, 0.32 mmol) in acetonitrile-water mixture (3 ml, $CH_3CN:H_2O::2:1$) under nitrogen atmosphere at 0° C. was added drop-wise a solution of ceric ammonium nitrate (480 mg, 0.88 mmol) in acetonitrile-water mixture (5 ml, $CH_3CN:H_2O::2:1$). It was stirred for 20 minutes at 0° C. (till completion of the reaction, TLC monitored). The solvent was removed in rotary evaporator and the residue dissolved in ethyl acetate. The ethyl acetate layer was washed with water, brine, dried with anhydrous $Na_2SO_4$ and the solvent evaporated to give the crude product as yellow oil. Purification of the oil over silica gel (60–120 mesh, 6–8% EtOAc in petroleum ether) afforded the pure compound (19) (90 mg, 90%) as a semi-solid.

IR(KBr): ν 2965.98, 1654.62, 1457.92, 1368.25, 1291.11, 1116.58, 1020.16, 841.78 $cm^{-1}$.

$^1$H NMR ($CDCl_3$, 300 MHz): δ 1.02 (3H, s), 1.36 (3H, s), 1.40 (3H, s), 1.79 (3H, s), 1.95 (1H, dd, J 5.0, 10.5 Hz), 2.24 (1H, d, J 19.9 Hz), 2.37–2.49 (2H, m), 3.16 (1, d, J 19.9 Hz), 6.63, 6.72 (2H, 2d, J 9.98), 6.82 (1H, br s).

EXAMPLE 20

Preparation of Compound of Formula (23)

To a stirred solution of (10) (50 mg, 0.08 mmol) in acetonitrile-water mixture (3 ml, $CH_3CN:H_2O::2:1$) under nitrogen atmosphere at 0° C., a solution of ceric ammonium nitrate (122 mg, 0.22 mmol) in acetonitrile-water mixture (4 ml, $CH_3CN:H_2O::2:1$) was added drop-wise. It was stirred for 20 minutes at 0° C. (till completion of the reaction, TLC monitored). The solvent was removed in rotary evaporator and the residue dissolved in ethyl acetate. The ethyl acetate layer was washed with water, brine, dried with anhydrous $Na_2SO_4$ and the solvent evaporated to give the crude product as yellow oil. Purification of the oil over silica gel (60–120 mesh, 10% ethyl acetate in petroleum ether) afforded the pure compound (23) (39 mg, 85%) as a foamy yellow solid.

m.p.: 90–92° C.

IR (KBr): ν 3443.28, 2978.52, 1740.44, 1702.84, 1654.62, 1601.59, 1455.03, 1372.10, 1289.18, 1254.47 $cm^{-1}$.

$^1$H NMR ($CDCl_3$, 300 MHz): δ 0.80 (3H, s), 1.17–1.25 (9H, br s), 1.31, 1.34 (6H, 2s), 1.61 (3H, s), 1.77 (3H, s), 1.82 (3H, s), 1.97 (1H, d, J 19.30 Hz), 2.17 (2H, br s), 2.74 (1H, d, J 19.30 Hz), 4.63 (1H, d, J 5.41 Hz), 5.15 (1H, br s), 5.45 (1H, bars), 5.61 (1H, bars), 6.60, 6.67 (2H, 2d, J 9.95 Hz, 9.96 Hz), 7.35–7.36 (5H, m).

EXAMPLE 21

Preparation of Compound of Formula (11)

To a well-stirred solution of (10) (45 mg, 0.072 mmol) in ethyl acetate (5 ml) under nitrogen atmosphere, HCl (2.5 ml, 4N solution) was added drop-wise at room temperature. The reaction mixture was then stirred at room temperature for 4 days (TLC monitored). Ammonia solution (7%) was then added drop-wise at 5° C. (ice cold condition) till the resulting solution was neutral and the resulting mixture was extracted with ethyl acetate. The ethyl acetate layer was washed with water, brine, dried over anhydrous $Na_2SO_4$ and the solvent evaporated under reduced pressure in a rotary evaporator to get the crude solid. The residue was chromatographed over silica gel (100–200 mesh, 50% ethyl acetate in petroleum ether) to afford the pure amino alcohol (11) (22 mg, 65%) as a white solid, which was crystallized from dry methanol.

m.p.: 178–179° C.

IR (KBr): ν 3358.43, 3294.79, 2945.73, 2684.43, 1725.98, 1592.91, 1457.93, 1254.47, 1183.11, 1078.98 $cm^{-1}$.

$^1$H NMR ($CDCl_3$, 300 MHz): δ 0.90 (3H, s), 1.38 (3H, s), 1.42 (3H, s), 1.57 (3H, s), 1.85–1.90 (2H, dd, J 5.31 Hz, 11.25 Hz), 2.03–2.33 (5H, m), 3.02 (1H, d, J 16.98 Hz), 3.69 (3H, s), 3.78 (3H, s), 4.51 (2H, d, J 12.45 Hz), 5.50–5.62 (2H, 2s), 6.63, 6.70 (2H, 2d, J 8.85 Hz, 8.91 Hz), 7.27–7.43 (3H, m), 7.49 (2H, d, J 7.44 Hz).

EXAMPLE 22

Preparation of Compound of Formula (24)

To a stirred solution of (11) (15 mg, 0.031 mmol) in acetonitrile-water mixture (2 ml, $CH_3CN:H_2O::2:1$) under nitrogen atmosphere at 0° C., a solution of ceric ammonium nitrate (54 mg, 0.093 mmol) in acetonitrile-water mixture (3 ml, $CH_3CN:H_2O::2:1$) was added drop-wise. It was stirred for 30 minutes at 0° C. (till completion of the reaction, TLC monitored). The solvent was removed in rotary evaporator and the residue dissolved in ethyl acetate. The ethyl acetate layer was washed with water, brine, dried with anhydrous $Na_2SO_4$ and the solvent evaporated to give the crude product as yellow oil. Purification of the oil over silica gel (100–200 mesh, 70% EtOAc in petroleum ether) afforded the pure quinone (24) (12 mg, 86%) as reddish brown solid.

m.p.: 164–165° C.

IR (KBr): ν 3399.89, 3247.00, 3046.00, 2920.66, 1737.55, 1651.73, 1600.63, 1457.92, 1386.57, 1293.04, 1188.90, 1094.41, 1018.23, 982.55, 840.81, 764.64, 701.96 $cm^{-1}$.

$^1$H NMR ($CDCl_3$, 300 MHz): δ 0.79 (3H, s), 1.02 (3H, s), 1.25 (3H, s), 1.29 (3H, s), 1.55–1.65 (2H, m), 1.74–1.89 (2H, m), 2.04–2.17 (4H, m), 2.73 (1H, d, J 19.33 Hz), 4.90–5.02 (2H, m), 5.25 (1H, s), 5.42 (1H, s), 6.50 (2H, t, J 10.37 Hz), 7.29–7.44 (3H, m), 7.69 (2H, J 6.57 Hz).

EXAMPLE 23

Preparation of Compound of Formula (12)

To a well-stirred solution of BOC-glycine (41 mg, 0.23 mmol) in $CH_2Cl_2$ (0.5 ml) under nitrogen atmosphere at 0° C., HOBT (63 mg, 0.46 mmol) was added followed by the addition of a solution of DCC (48 mg, 0.23 mmol) and DMAP (28 mg, 0.23 mmol) in $CH_2Cl_2$ (1 ml). The reaction mixture was stirred at 0° C. for 1 h and then at room temperature for 1 h. The reaction mixture was cooled to 0° C. and a solution of (8) (49 mg, 0.155 mmol) in $CH_2Cl_2$ (0.5 ml) were then added. The reaction mixture stirred at room temperature for 2 days. The solvent was removed under reduced pressure in a rotary evaporator. The residue was then chromatographed over silica gel (100–200 mesh, 6% ethyl acetate in petroleum ether) to give the ester (12) (50 mg, 70%) as a white foamy solid.

m.p.: 148–150° C.

IR (KBr): ν 3384, 2974, 2838, 1704, 1593, 1517, 1459, 1436, 1337, 1251, 1165, 1059 $cm^{-1}$.

$^1$H NMR ($CDCl_3$, 300 MHz): δ 0.90 (3H, s), 1.38 (3H, s), 1.42 (3H, s), 1.47 (9H, s), 1.59 (3H, s), 1.87 (1H, dd, J 5.3 & 11.3 Hz), 2.12–2.32 (3H, m), 3.01 (1H, d, J 17 Hz), 3.73 (3H, s), 3.78 (3H, s), 4.06 (2H, d, J 4.8 Hz), 5.10 (1H, bars), 5.46 (1H, bars), 5.61 (1H, bars), 6.68 (2H, 2×d, J 8.9 Hz).

EXAMPLE 24

Preparation of Compound of Formula (13)

To a well-stirred solution of BOC-phenyl alanine (24 mg, 0.088 mmol) in $CH_2Cl_2$ (0.5 ml) under nitrogen atmosphere at 0° C., HOBT (24 mg, 0.175 mmol) was added followed by the addition of a solution of DCC (24 mg, 0.114 mmol) and DMAP (11 mg, 0.316 mmol) in $CH_2Cl_2$ (1 ml). The reaction mixture was stirred at 0° C. for 1 h and then at room temperature for 1 h. The reaction mixture was cooled to 0° C. and a solution of (8) (100 mg, 0.316 mmol) in $CH_2Cl_2$ (1 ml) added. The reaction mixture stirred at room temperature for 2 days. The solvent was evaporated under reduced pressure in a rotary evaporator. The residue was chromatographed over silica gel (100–200 mesh, 5% ethyl acetate in petroleum ether) to give the ester (13) (21 mg, 75% with respect to recovered starting material) as a white foamy solid.

m.p.: 66–68° C.

IR(KBr): ν 3438, 2976, 1718, 1595, 1497, 1457, 1365, 1254, 1168, 1061, 795, 701 cm$^{-1}$.

$^1$H NMR(300 MHz, CDCl$_3$): δ 0.87 (3H, s), 1.38–1.42 (15H, m), 1.55 (3H, s), 1.88 (1H, dd, J 5.55 and 11.2 Hz), 2.12–2.24 (3H, m), 3.04–3.12 (2H, m), 3.29–3.36 (1H, m) 3.68 (3H, s), 3.79 (3H, s), 4.70–4.72(1H, m), 4.96 (1H, bd, J 8.40 Hz) 5.46 (1H, bars), 5.59 (1H, bars), 6.68 (2H, 2×d, J 8.8 & 21.75 Hz), 7.16–7.29 (5H, m).

EXAMPLE 25

Preparation of Compound of Formula (14)

To a well-stirred solution of BOC-valine (103 mg, 0.474 mmol) in $CH_2Cl_2$ (1 ml) under nitrogen atmosphere at 0° C., HOBT (129 mg, 0.949 mmol) was added followed by the addition of a solution of DCC (98 mg, 0.474 mmol) and DMAP (39 mg, 0.316 mmol) in $CH_2Cl_2$ (1 ml). The reaction mixture was stirred at 0° C. for 1 h and then at room temperature for 1 h. The reaction mixture was cooled to 0° C. and a solution of (8) (100 mg, 0.316 mmol) in $CH_2Cl_2$ (1 ml) added. The reaction mixture stirred at room temperature for 2 days. The solvent was evaporated under reduced pressure in a rotary evaporator. The residue was chromatographed over silica gel (100–200 mesh, 5% ethyl acetate in petroleum ether) to give the ester (14) (130 mg, 89% with respect to recovered starting material) as a white foamy solid.

m.p.: 85–87° C.

IR(KBr): ν 3377, 2959, 1720, 1461, 1365, 1253, 1162, 1074 cm$^{-1}$.

$^1$H NMR(300 MHz, CDCl$_3$): δ 0.92 (3H, s), 1.02 (3H, d, J 7 Hz), 1.09 (3H, d, J 7 Hz), 1.38 (3H, s), 1.42 (3H, s), 1.45 (9H, s), 1.59 (3H, s), 1.86–1.91 (1H, m), 2.14 (2H, d, J 17 Hz), 2.23–2.38 (2H, m), 3.05 (1H, d, J 17 Hz), 3.68 (3H, s), 3.78 (3H, s), 4.35–4.38 (1H, m), 5.07–5.10 (1H, m), 5.46 (1H, s), 5.60 (1H, bars), 6.63 (1H, d, J 9 Hz), 6.70 (1H, d, J 9 Hz).

EXAMPLE 26

Preparation of Compound of Formula (7)

To a well-stirred solution of (6) (58 mg, 0.095 mmol) in ethyl acetate (4 ml) under nitrogen atmosphere, HCl (3 ml, 4N solution) was added drop-wise at room temperature. The reaction mixture was then stirred at room temperature for 4 days (TLC monitored). Ammonia solution (7%) was then added drop-wise at 5° C. (ice cold condition) till the resulting solution was neutral and the resulting mixture was extracted with ethyl acetate. The ethyl acetate layer was washed with water, brine, dried over anhydrous Na$_2$SO$_4$ and the solvent evaporated under reduced pressure in a rotary evaporator to get the crude solid. The residue was chromatographed over silica gel (100–200 mesh, 50% ethyl acetate in petroleum ether) to afford the pure amino alcohol (7) (30 mg, 68%) as a white solid.

m.p.: 72–75° C.

IR (KBr): ν 3374.82, 2929.34, 1733.69, 1458.89, 1253.50, 1069.33, 701.96 cm$^{-1}$.

$^1$H NMR (CDCl$_3$, 300 MHz): δ 1.38 and 1.41 (2×3H, s), 1.64 (3H, brs), 1.31–2.75 (several protons, m) 3.76 and 3.77 (2×3H, s), 4.43–4.50 (2H, m), 5.58 (1H, brs), 5.70 (1H, brs), 6.63 (1H, d, J 8.8 Hz), 6.69 (1H, d, J 8.9 Hz), 7.27–7.47 (5H, m).

EXAMPLE 27

Preparation of Compound of Formula (15)

To a well stirred solution of compound (8) (100 mg, 0.316 mmol), pyridine (30 mg, 30 µL, 1.2 eqv.) in dry dichloromethane (10 ml) was added drop-wise 2,6-dichloropyrimidine-4-carbonyl chloride (70 mg, 0.331 mmol) in dichloromethane (4 ml) under ice-water bath (5–10° C.) condition. After addition, the reaction mixture was further stirred at room temperature for 12 h, until the reaction was completed (TLC). After completion, the reaction mixture was diluted with dichloromethane and washed with brine (2×5 ml), dried over anhydrous Na$_2$SO$_4$. Solvent was evaporated to give crude product. The crude product was chromatographed over silica gel (60–120 mesh, 4% ethylacetate-petroleum ether as eluent) to afford the ester (15) (108 mg, 70%) as yellow solid.

m.p.: 161–164° C.

IR (KBr): ν 2946, 2836, 1725, 1594, 1534, 1463, 1391, 1314, 1253, 1068, 833, 724 cm$^{-1}$ $^1$H NMR (CDCl$_3$, 300 MHz): δ 1.04 (3H, s), 1.42 (3H, s), 1.44 (3H, s), 1.61 (3H, s), 1.94 (1H, dd, J 5 & 11 Hz), 2.21–2.30 (3H, m), 3.04 (1H, d, J 17 Hz), 3.68 (3H, s), 3.79 (3H, s), 5.72 (2H, brs), 6.64 & 6.72 (2H, 2×d, J 9 Hz), 7.97 (1H, s).

EXAMPLE 28

Preparation of Compound of Formula (27)

To a stirred solution of (15) (40 mg, 0.08 mmol) in acetonitrile-water mixture-(3 ml, CH$_3$CN:H$_2$O::2:1) under nitrogen atmosphere at 0° C. was added drop-wise a solution of ceric ammonium nitrate (134 mg, 0.244 mmol) in acetonitrile-water mixture (3 ml, CH$_3$CN:H$_2$O::2:1). It was stirred for 25 minutes at 0° C. (till completion of the reaction, TLC monitored). The solvent was removed in rotary evaporator and the residue dissolved in ethyl acetate. The ethyl acetate layer was washed with water, brine, dried with anhydrous Na$_2$SO$_4$ and the solvent evaporated to give the crude product as yellow oil. Purification of the oil over silica gel (60–120 mesh, 10% EtOAc in petroleum ether) afforded the pure compound (27) (36 mg, 81%) as a yellow solid.

m.p.: 137–140° C.

IR (KBr): ν 2978, 1727, 1652, 1532, 1318, 1255, 1195, 837 cm$^{-1}$ $^1$H NMR (CDCl$_3$, 300 MHz): δ 1.05 (3H, s), 1.36 (3H, s), 1.38 (3H, s), 1.61 (3H, s), 1.83 (1H, dd, J 5 & 11 Hz), 2.07 (1H, d, J 19 Hz), 2.22–2.78 (2H, m), 2.81 (1H, d, J 19 Hz), 5.68 (1H, s), 6.62 & 6.68 (2H, 2×d, J 9 Hz), 7.97 (1H, s).

EXAMPLE 29

Preparation of Compound of Formula (21)

To a stirred solution of compound of formula (8) (35 mg, 0.11 mmol) in acetonitrile-water mixture (4 ml, CH$_3$CN:H$_2$O::2:1) under nitrogen atmosphere at 0° C., a solution of ceric ammonium nitrate (183 mg, 0.33 mmol) in acetonitrile-water mixture (2 ml, CH$_3$CN:H$_2$O::2:1) was added drop-wise. It was stirred for 25 minutes at 0° C. (till completion of the reaction, TLC monitored). The solvent was removed in rotary evaporator and the residue dissolved in ethyl acetate. The ethyl acetate layer was washed with water, brine, dried with anhydrous Na$_2$SO$_4$ and the solvent evaporated to give the crude product as an yellow oil. Purification of the oil over silica gel (60–120 mesh, 15% EtOAc in petroleum ether) afforded the pure compound (21) (26 mg, 84%) as yellow solid.

m.p.: 134–137° C.

$R_1$=absorbance of control sample at 540 nm.

The IC$_{50}$ Values of the cytotoxicity defined as the concentration at which 50% of the cells are killed in vitro was calculated for each cell line treated with each of the anthracene based compounds.

The IC$_{50}$ values of in vitro cytotoxicity of seven anthracene based compounds are shown in the Table 1.

TABLE 1

| | | ED$_{50}$ ug/ml | | | | | | | | | | |
|---|---|---|---|---|---|---|---|---|---|---|---|---|
| S No | Compound No. | MOLT4 Leukemia | HT29 Colon | DU145 Prostate | KB Oral | L132 Lung | MiaPaca2 Pancreatic | Hep2 Larynx | PA1 Ovarian | ECV304 Endothelial | MCF7 Breast | U87MG Glioblastoma | PTC Colon |
| 1 | 7 | 5.0 | 8.0 | 33 | 29 | 24 | 35 | 5.0 | 5.0 | 6.0 | 35 | 24 | 5.0 |
| 2 | 11 | <1 | 27 | 10 | 18 | 21 | 7 | 16 | 4 | 2 | 8 | 10 | ND |
| 3 | 29 | 5.0 | 6.5 | 34 | 30 | 5.0 | 35 | 5.0 | 5.0 | 9.0 | 29 | 8.0 | 5.0 |
| 4 | 19 | 4 | 33 | 15 | 62 | 6 | 80 | 26 | 15 | 6 | 18 | 16 | 40 |
| 5 | 24 | 7 | 6 | 5 | 6.6 | >100 | >100 | 14 | 8 | 3 | >100 | 5 | ND |
| 6 | 25 | <1 | 35 | 32 | 35 | 4 | 35 | 11 | 8 | 5 | 16 | 24 | 8 |
| 7 | 26 | 5.0 | 6.5 | 26 | 31 | 10 | 35 | 20 | 19 | 29 | 32 | 24 | 5.0 |

IR (KBr): ν 3570.56, 1647.87, 1597.73, 1456.96, 1390.42, 1366.32, 1294.00, 1172.51, 1118.51, 1095.37, 1061.62, 1035.59 cm$^{-1}$ $^1$H NMR (CDCl$_3$, 300 MHz): δ 0.85 (3H, s), 1.32 (3H, s), 1.35 (3H, s), 1.65 (1H, dd, J 5.6 & 11.2 Hz), 1.73 (3H, s), 2.00 (1H, d, J 19.3 Hz), 2.08–2.16 (3H, m), 3.09 (1H, d, J 19.3 Hz), 3.88 (1H, s), 5.52 (1H, s), 6.62 (1H, d, J 9.9 Hz), 6.70 (1H, d, J 9.9 Hz).

EXAMPLE 30

In Vitro Cytotoxicity of the Anthracene Based Compounds

A number of the anthracene based compounds were tested for cytotoxicity against 12 human tumor cell lines. Briefly, a three day MTT cytotoxicity assay was performed, which is based on the principle of uptake of MTT (3-(4,5-dimethylthiazol-2-yl)-2,5-diphenyl tetrazolium bromide), a tetrazolium salt, by the metabolically active cells where it is metabolized by active mitochondria into a blue colored formazan product that is read spectrophotometrically. MTT was dissolved in phosphate buffered saline with a pH of 7.4 to obtain an MTT concentration of 5 mg/ml; the resulting mixture was filtered through a 0.22 micron filter to sterilize and remove a small amount of insoluble residue. For each type of tumor cell, 10,000 to 15,000 cells were seeded in a 96-well culture plate and incubated with the individual anthracene based compounds in a CO$_2$ incubator for a total of 72 hours. Control cells not treated with the anthracene based compounds were similarly incubated. The assay was terminated by adding 100 ug (20 ul) of MTT to each well, then incubating for additional one hour, and finally adding 50 ul of 10% SDS-0.01N HCl to each well to lyse the cells and dissolve formazan. After incubating for one hour, the plate was read spectrophotometrically at 540 nm and the percentage of cytotoxicity calculated using the following formula:

Cytotoxicity percentage=100×[1−(X/R$_1$)], where X=(absorbance of treated sample at 540 nm)−(absorbance of blank at 540 nm)

What is claimed is:

1. A compound of formula (1)

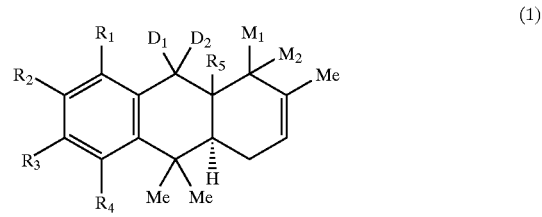

(1)

wherein

R$_1$ to R$_4$ are the same or different and represent hydrogen, alkyl, hydroxy, alkoxy, methoxymethyloxy, alkylthio, amino, alkylamino, dialkylamino, alkylcarbonyloxy, NHCOCH$_3$, NHCOCF$_3$, NH-alkyl, N-dialkyl wherein the alkyl groups may be the same or different or a methylenedioxy group is fused in lieu of either R$_1$, R$_2$ or R$_2$, R$_3$ or R$_3$, R$_4$ position, respectively;

R$_5$ is hydrogen, alkyl or alkoxycarbonyl;

M$_1$ is hydrogen, and M$_2$ is WR$_6$ or M$_1$ and M$_2$ together represent X;

W is oxygen or NH;

R$_6$ is hydrogen, alkyl, alkylcarbonyl, tosyl, COCH(R$_7$)NHR$_8$, COCH(OR$_9$)CH(NHR$_8$)phenyl, 2,2-Dimethyl-4-phenyloxazolidine-5-carbonyl or 3-substituted-2,2-dimethyl-4-phenyloxazolidine-5-carbonyl, where 3-substitutents are selected from the group consisting of CO(O-alkyl), CO(O-benzyl) and benzoyl;

2,6-Dioxo-1,2,3,6-tetrahydro-4-carbonyl, 2,6-disubstituted pyrimidine-4-carbonyl wherein the substituents are the same or different and are selected from the group consisting of chloro, fluoro, amino, NH-alkyl, N-dialkyl wherein the alkyl groups are the same or different; NH-aryl; and NH—CH$_2$-aryl 4-morpholino, 1-piperidino or 1-pyrolidino;

R$_7$ is hydrogen, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl;

$R_8$ is hydrogen, $COCH_3$, $COCF_3$, benzoyl or tert.-butyloxycarbonyl, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl;

$R_9$ is hydrogen, $COCH_3$, $COCF_3$, benzoyl or tert.-butyloxycarbonyl $D_1$ is H and $D_2$ is hydrogen, hydroxy or OAc; or $D_1$ and $D_2$ together are carboxy, $NOR_{10}$, or $NR_{11}$ X, represents $NOR_{10}$ or $NR_{11}$;

$R_{10}$ is hydrogen or alkyl; and $R_{11}$ is alkyl, benzyl, phenyl, 2 or 3 or 4-alkoxyphenyl, 2 or 3 or 4-fluorophenyl, 2 or 3 or 4-bromophenyl, 2,3 or 2,4 or 3,4 or 3,5-dialkoxyphenyl; or a salt thereof.

2. A compound of formula (2)

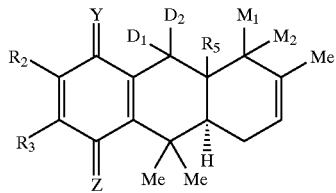

(2)

wherein $R_2$ and $R_3$ are the same or different and represent hydrogen, alkyl, hydroxy, alkoxy, methoxymethyloxy, alkylthio, amino, alkylamino, dialkylamino, alkylcarbonyloxy, $NHCOCH_3$, $NHCOCF_3$, NH-alkyl, N-dialkyl wherein the alkyl groups are the same or different or a methylenedioxy group fused in lieu of $R_2$, $R_3$;

$R_5$ is hydrogen, alkyl or alkoxycarbonyl;

$M_1$ is hydrogen, and $M_2$ is $WR_6$ or $M_1$ and $M_2$ together represent X;

W is oxygen or NH;

$R_6$ is hydrogen, alkyl, alkylcarbonyl, tosyl, $COCH(R_7)NHR_8$, $COCH(OR_9)CH(NHR_8)$phenyl, 2,2-Dimethyl-4-phenyloxazolidine-5-carbonyl or 3-substituted-2,2-dimethyl-4-phenyloxazolidine-5-carbonyl, wherein the 3-substitutents are selected from the group consisting of CO(O-alkyl), CO(O-benzyl) and benzoyl;

2,6-Dioxo-1,2,3,6-tetrahydro-4-carbonyl, or 2,6-disubstituted pyrimidine-4-carbonyl wherein the substituents are the same or different and are selected from the group consisting of chloro, fluoro, amino, NH-alkyl, N-dialkyl the alkyl groups are the same or different NH-aryl and NH—$CH_2$-aryl 4-morpholino, 1-piperidino or 1-pyrolidino;

$R_7$ is hydrogen, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl;

$R_8$ is hydrogen, $COCH_3$, $COCF_3$, benzoyl or tert.-butyloxycarbonyl, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl;

$R_9$ is hydrogen, $COCH_3$ or $COCF_3$, benzoyl or tert.-butyloxycarbonyl;

$D_1$ is H and $D_2$ is hydrogen, hydroxy or OAc or $D_1$ and $D_2$ together are carboxy, $NOR_{10}$, or $NR_{11}$;

X, Y and Z are the same or different and represent oxygen, $NOR_{10}$ or $NR_{11}$;

$R_{10}$ is hydrogen or alkyl; and $R_{11}$ is alkyl, benzyl, phenyl, 2 or 3 or 4-alkoxyphenyl, 2 or 3 or 4-fluorophenyl, 2 or 3 or 4-bromophenyl, 2,3 or 2,4 or 3,4 or 3,5-dialkoxyphenyl; or a salt thereof.

3. A compound of formula (3)

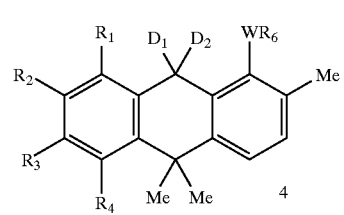

(3)

wherein $R_1$ to $R_4$ are the same or different and represent hydrogen, alkyl, hydroxy, alkoxy, methoxymethyloxy, alkylthio, amino, alkylamino, dialkylamino, alkylcarbonyloxy, $NHCOCH_3$, $NHCOCF_3$, NH-alkyl, N-dialkyl wherein the alkyl groups are the same or different or a methylenedioxy group fused in lieu of either $R_1$, $R_2$ or $R_2$, $R_3$ or $R_3$, $R_4$ position, respectively;

W is oxygen or NH;

$R_6$ is hydrogen, alkyl, alkylcarbonyl, tosyl, $COCH(R_7)NHR_8$, $COCH(OR_9)CH(NHR_8)$phenyl, 2,2-Dimethyl-4-phenyloxazolidine-5-carbonyl or 3-substituted-2,2-dimethyl-4-phenyloxazolidine-5-carbonyl, wherein the 3-substitutents are selected from the group consisting of CO(O-alkyl), CO(O-benzyl) and benzoyl;

2,6-Dioxo-1,2,3,6-tetrahydro-4-carbonyl, or 2,6-disubstituted pyrimidine-4-carbonyl wherein the substituents are the same or different and are selected from the group consisting of chloro, fluoro, amino, NH-alkyl, N-dialkyl, NH-aryl, NH—$CH_2$-aryl 4-morpholino, 1-piperidino or 1-pyrolidino;

$R_7$ is hydrogen, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl;

$R_8$ is hydrogen, $COCH_3$, $COCF_3$, benzoyl or tert.-butyloxycarbonyl, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl;

R$_9$ is hydrogen, COCH$_3$ or COCF$_3$, benzoyl or tert.-butyloxycarbonyl;

D$_1$ is H and D$_2$ is hydrogen, hydroxy or OAc or D$_1$ and D$_2$ together as carboxy, NOR$_{10}$, or NR$_{11}$;

R$_{10}$ is hydrogen or alkyl; and

R$_{11}$ is alkyl, benzyl, phenyl, 2 or 3 or 4-alkoxyphenyl, 2 or 3 or 4-fluorophenyl, 2 or 3 or 4-bromophenyl, 2,3 or 2,4 or 3,4 or 3,5-dialkoxyphenyl; or a salt thereof.

4. A compound according to claim 1, wherein the linear six-six-six tricyclic ring systems are tetramethyl-tetrahydro-anthracenone, trimethyl-tetrahydro-anthracenone, tetramethyl-hexahydro-anthracenol, trimethyl-hexahydro-anthracenol, trimethyl-dihydro-anthracenol, tetramethyl-tetrahydro-anthracenetrione, trimethyl-tetrahydro-anthracenetrione, hydroxy-tetramethyl-tetrahydro-anthracenedione or hydroxy-trimethyl-hexahydro-anthracenedione.

5. A compound according to claim 1, of the formula (4)

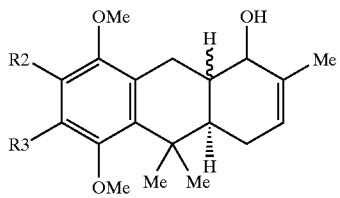

4

5,8-Dimethoxy-2,10,10,-trimethyl-1,4,4a,9,9a,10-hexahydro-anthracen-1-ol R$_2$=R$_3$=H or or a derivative thereof where R$_2$, and R$_3$ are the same or different and represent hydroxy, alkoxy, methoxymethyloxy, alkylthio, amino, alkylamino, dialkylamino, alkylcarbonyloxy, NHCOCH$_3$, NHCOCF$_3$, NH-alkyl, N-dialkyl wherein the alkyl groups are the same or different or a methylenedioxy group is fused in lieu of R$_2$, R$_3$ position, or a salt thereof.

6. A compound according to claim 1, of formula (5)

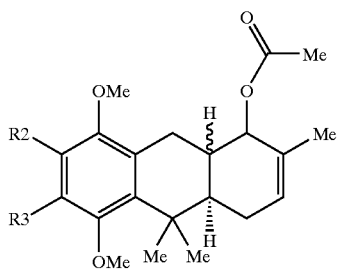

5

Acetic acid 5,8-dimethoxy-2,10,10-trimethyl-1,4,4a,9,9a,10-hexahydro-anthracene-1-yl ester where R$_2$=R$_3$=H or a derivative thereof where R$_2$, and R$_3$ are the same or different and represent hydroxy, alkoxy, methoxymethyloxy, alkylthio, amino, alkylamino, dialkylamino, alkylcarbonyloxy, NHCOCH$_3$, NHCOCF$_3$, NH-alkyl, N-dialkyl wherein the alkyl groups are the same or different or a methylenedioxy group in lieu of R$_2$, R$_3$ position; or a salt thereof.

7. A compound according to claim 1, of formula (6)

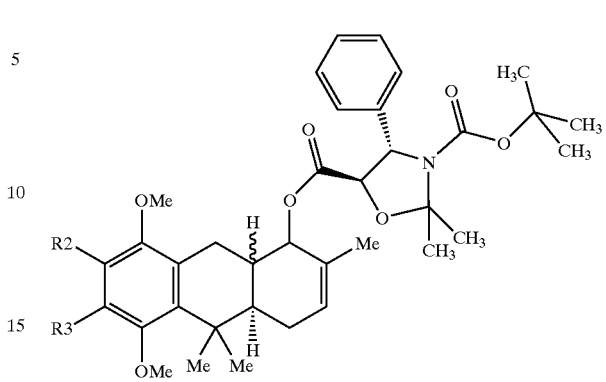

6

2,2-Dimethyl-4-phenyl-oxazolidine-3,5-dicarboxylic acid 3-tert-butyl ester 5-(5,8-dimethoxy-2,10,10-trimethyl-1,4,4a,9,9a,10-hexahydro-anthrcen-1-yl) ester where R$_2$=R$_3$=H or a derivative thereof where R$_2$, and R$_3$ are the same or different and represent hydroxy, alkoxy, methoxymethyloxy, alkylthio, amino, alkylamino, dialkylamino, alkylcarbonyloxy, NHCOCH$_3$, NHCOCF$_3$, NH-alkyl, N-dialkyl wherein the alkyl groups are the same or different or a methylenedioxy group fused in lieu of R$_2$, R$_3$ position; or a salt thereof.

8. A compound according to claim 1 of formula (7)

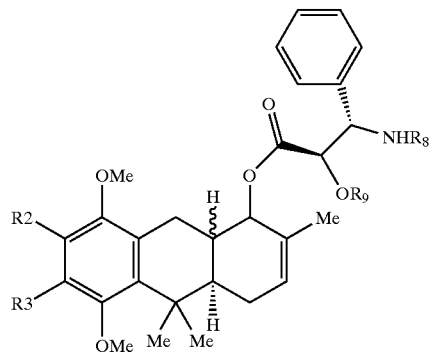

7

3-Amino-2-hydroxy-3-phenyl-propionic acid 5,8-dimethoxy-2,10,10-trimethyl-1,4,4a,9,9a,10-hexahydro-anthracen-1-yl ester where R$_2$=R$_3$=R$_8$=R$_9$=H or a derivative thereof where R$_2$, and R$_3$ are the same or different and represent hydrogen, hydroxy, alkoxy, methoxymethyloxy, alkylthio, amino, alkylamino, dialkylamino, alkylcarbonyloxy, NHCOCH$_3$, NHCOCF$_3$, NH-alkyl, N-dialkyl wherein the alkyl groups are the same or different or a methylenedioxy group fused in lieu of R$_2$, R$_3$ position;

R$_8$ is COCH$_3$, COCF$_3$, benzoyl or tert.-butyloxycarbonyl, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl; and R$_9$ is COCH$_3$, COCF$_3$, benzoyl or tert.-butyloxycarbonyl. or a salt thereof.

9. A compound according to claim 1 of formula (8)

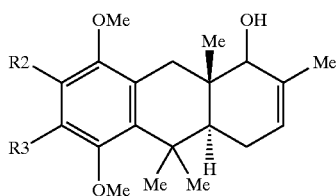

5,8-Dimethoxy-2,9a,10,10-tetramethyl-1,4,4a,9,9a,10-hexahydro-anthracen-1-ol $R_2$=$R_3$=H or a derivative thereof where $R_2$, and $R_3$ are the same or different and represent hydroxy, alkoxy, methoxymethyloxy, alkylthio, amino, alkylamino, dialkylamino, alkylcarbonyloxy, NHCOCH$_3$, NHCOCF$_3$, NH-alkyl, N-dialkyl wherein the alkyl groups may be the same or different, or methylenedioxy group is fused in lieu of $R_2$, $R_3$ position, or a salt thereof.

10. A compound according to claim 1 of formula (9)

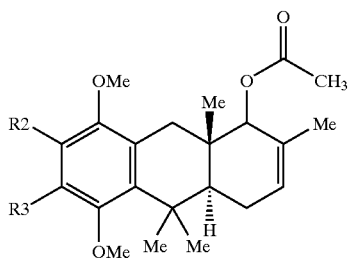

Acetic acid 5,8-dimethoxy-2,9a,10,10-tetramethyl-1,4,4a,9,9a,10-hexahydro-anthracen-1-yl ester where $R_2$=$R_3$=H or a derivative thereof where $R_2$, and $R_3$ are the same or different and represent hydroxy, alkoxy, methoxymethyloxy, alkylthio, amino, alkylamino, dialkylamino, alkylcarbonyloxy, NHCOCH$_3$, NHCOCF$_3$, NH-alkyl, N-dialkyl wherein the alkyl groups are the same or different or a methylenedioxy group fused in lieu of $R_2$, $R_3$ position; or a salt thereof.

11. A compound according to claim 1 of formula (10)

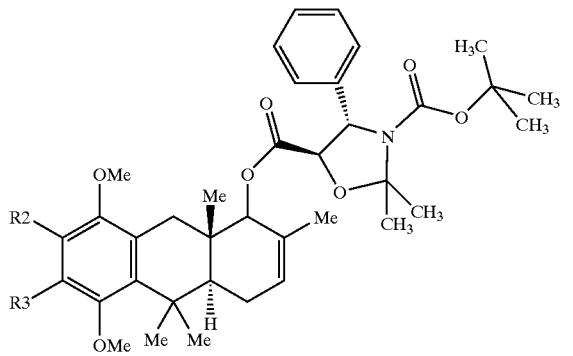

2,2-Dimethyl-4-phenyl-oxazolidine-3,5-dicarboxylic acid 3-tert-butyl ester 5-(5,8-dimethoxy-2,9a,10,10-tetramethyl-1,4,4a,9,9a,10-hexahydro-anthrcen-1-yl) ester where $R_2$=$R_3$=H or a derivative thereof where $R_2$, and $R_3$ are the same or different and represent hydroxy, alkoxy, methoxymethyloxy, alkylthio, amino, alkylamino, dialkylamino, alkylcarbonyloxy, NHCOCH$_3$, NHCOCF$_3$, NH-alkyl, N-dialkyl wherein the alkyl groups are the same or different, or a methylenedioxy group fused in lieu of $R_2$, $R_3$ position; or a salt thereof.

12. A compound according to claim 1 of formula (11)

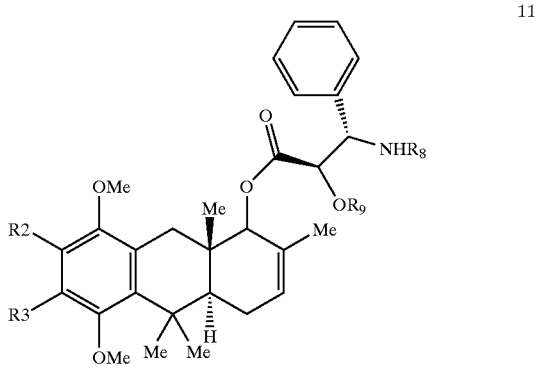

3-Amino-2-hydroxy-3-phenyl-propionic acid 5,8-dimethoxy-2,9a,10,10-tetramethyl-1,4,4a,9,9a,10-hexahydro-anthrcen-1-yl ester where $R_2$=$R_3$=H or a derivative thereof where $R_2$, and $R_3$ are the same or different and represent hydrogen, hydroxy, alkoxy, methoxymethyloxy, alkylthio, amino, alkylamino, dialkylamino, alkylcarbonyloxy, NHCOCH$_3$, NHCOCF$_3$, NH-alkyl, N-dialkyl wherein the alkyl groups are the same or different, or a methylenedioxy group fused in lieu of $R_2$, $R_3$ position;

$R_8$ is COCH$_3$, COCF$_3$, benzoyl or tert.-butyloxycarbonyl, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl; and $R_9$ is COCH$_3$, COCF$_3$, benzoyl or tert.-butyloxycarbonyl or a salt thereof.

13. A compound according to claim 1 of formula (12)

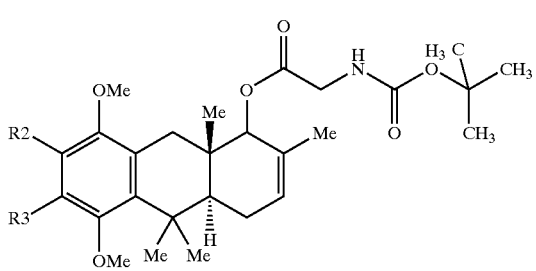

tert-Butoxycarbonylamino-acetic acid 5,8-dimethoxy-2,9a,10,10-tetramethyl-1,4,4a,9,9a10-hexahydro-anthracen-1-yl ester where $R_2$=$R_3$=H or a derivative thereof where $R_2$, and $R_3$ are the same or different and represent hydroxy, alkoxy, methoxymethyloxy, alkylthio, amino, alkylamino, dialkylamino, alkylcarbonyloxy, NHCOCH$_3$, NHCOCF$_3$, NH-alkyl, N-dialkyl wherein the alkyl groups are the same or different or a methylenedioxy group fused in lieu of $R_2$, $R_3$ position; or a salt thereof.

14. A compound according to claim 1 of formula (13)

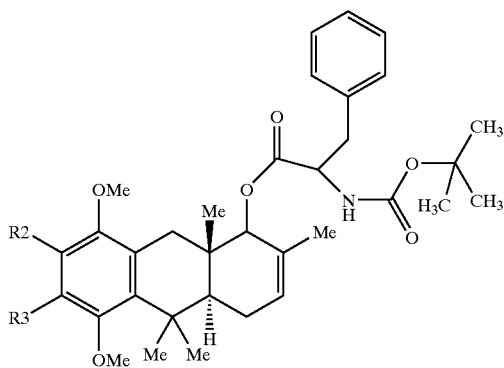

13

2-tert-Butoxycarbonylamino-3-phenyl-propionic acid 5,8-dimethoxy-2,9a,10,10-tetramethyl-1,4,4a,9,9a,10-hexahydro-anthracen-1-yl ester where $R_2=R_3=H$ or a derivative thereof where $R_2$, and $R_3$ are the same or different and represent hydroxy, alkoxy, methoxymethyloxy, alkylthio, amino, alkylamino, dialkylamino, alkylcarbonyloxy, NHCOCH$_3$, NHCOCF$_3$, NH-alkyl, N-dialkyl wherein the alkyl groups are the same or different, or a methylenedioxy group fused in lieu of $R_2$, $R_3$ position; or a salt thereof.

15. A compound according to claim 1 of formula (14)

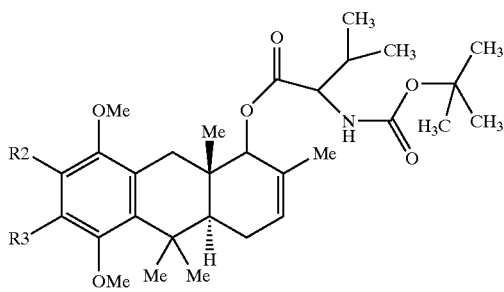

14

2-tert-Butoxycarbonylamino-3-methyl-butyricacid 5,8-dimethoxy-2,9a,10,10-tetramethyl-1,4,4a,9,9a,10-hexahydr-anthracen-1-yl ester where $R_2=R_3=H$ or a derivative thereof where $R_2$, and $R_3$ are the same or different and represent hydroxy, alkoxy, methoxymethyloxy, alkylthio, amino, alkylamino, dialkylamino, alkylcarbonyloxy, NHCOCH$_3$, NHCOCF$_3$, NH-alkyl, N-dialkyl wherein the alkyl groups are the same or different, or a methylenedioxy group fused in lieu of $R_2$, $R_3$ position; or a salt thereof.

16. A compound according to claim 3 of formula (28)

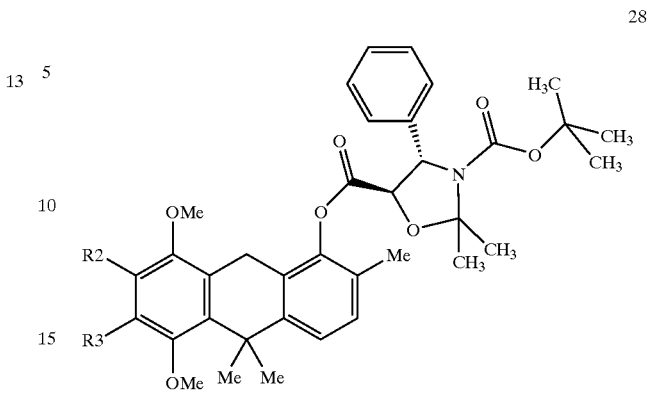

28

2,2-Dimethyl-4-phenyl-oxazolidine-3,5-dicarboxylic acid 3-tert-butyl ester 5-(5,8-dimethoxy-2,10,10-trimethyl-9,10-dihydro-anthracen-1-yl) ester where $R_2=R_3=H$ or a derivative thereof where $R_2$, and $R_3$ are the same or different and represent hydrogen, hydroxy, alkoxy, methoxymethyloxy, alkylthio, amino, alkylamino, dialkylamino, alkylcarbonyloxy, NHCOCH$_3$, NHCOCF$_3$, NH-alkyl, N-dialkyl wherein the alkyl groups are the same or different, or a methylenedioxy group fused in lieu of $R_2$, $R_3$ position; or a salt thereof.

17. A compound according to claim 1 of formula (15)

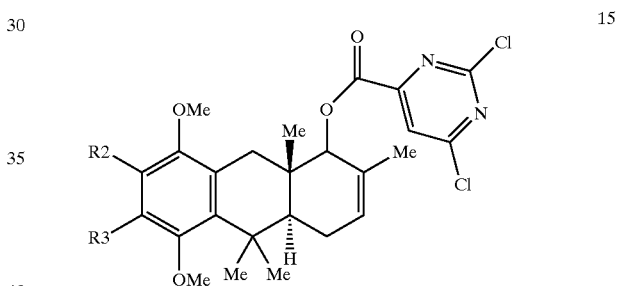

15

2,6-Dichloro-pyrimidine-4-carboxylicacid-5,8-dimethoxy-2,9a,10,10-tetramethyl-1,4,4a,9,9a,10-hexahydro-anthracen-1-yl ester where $R_2=R_3=H$ or a derivative thereof where $R_2$, and $R_3$ are the same or different and represent hydroxy, alkoxy, methoxymethyloxy, alkylthio, amino, alkylamino, dialkylamino, alkylcarbonyloxy, NHCOCH$_3$, NHCOCF$_3$, NH-alkyl, N-dialkyl wherein the alkyl groups are the same or different, or a methylenedioxy group fused in lieu of $R_2$, $R_3$ position; or a salt thereof.

18. A compound according to claim 3 of formula (29)

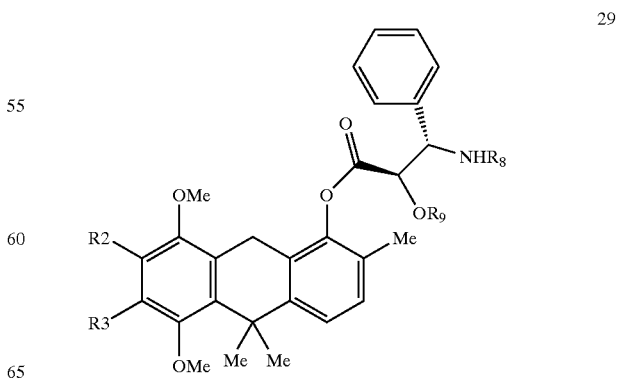

29

3-Amino-2-hydroxy-3-phenyl-propionic acid 5,8-dimethoxy-2,10,10,-trimethyl-9,10-dihydro-anthracen-1-yl ester where $R_2=R_3=H$ or a derivative thereof where $R_2$, and $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl, N-dialkyl wherein the alkyl groups are the same or different, or a methylenedioxy group fused in lieu of $R_2$, $R_3$ position;

$R_8$ is $COCH_3$, $COCF_3$, benzoyl or tert.-butyloxycarbonyl, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl; and $R_9$ is $COCH_3$, $COCF_3$, benzoyl or tert.-butyloxycarbonyl or a salt thereof.

19. A compound according to claim 1 of formula (16)

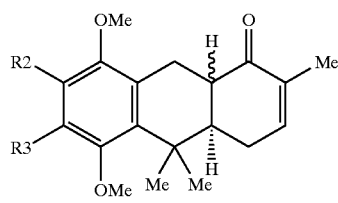

16

5,8-Dimethoxy-2,10,10-trimethyl-4a,9,9a,10-tetrahydro-4H-anthracen-1-one where $R_2=R_3=H$ or a derivative thereof where $R_2$, and $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl, N-dialkyl wherein the alkyl groups are the same or different, or a methylenedioxy group fused in lieu of $R_2$, $R_3$ position; or a salt thereof.

20. A compound according to claim 1 of formula (17)

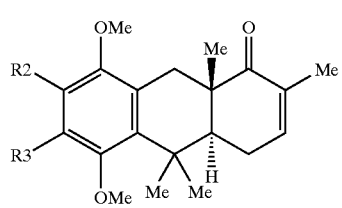

17

5,8-Dimethoxy-2,9a,10,10-tetramethyl-4a,9,9a,10-tetrahydro-4H-anthracen-1-one where $R_2=R_3=H$ or a derivative thereof where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-, N-dialkyl wherein the alkyl groups are the same or different, or a methylenedioxy group fused in lieu of $R_2$, $R_3$ position; or a salt thereof.

21. A compound according to claim 1 of formula (18)

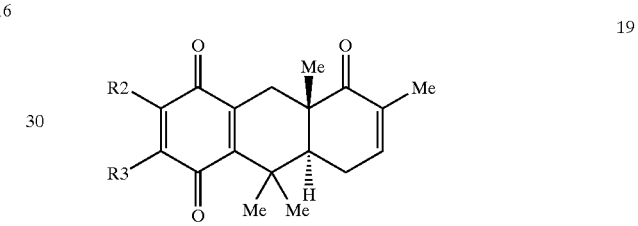

18

5,8-Dimethoxy-2,10,20,-trimethyl-4a,9,9a,10-tetrahydro-4H-anthracen-1-one oxime where $R_2=R_3=H$ or a derivative thereof where $R_2$, and $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl, N-dialkyl wherein the alkyl groups are the same or different, or a methylenedioxy group fused in lieu of $R_2$, $R_3$ position; or a salt thereof.

22. A compound according to claim 2 of formula (19)

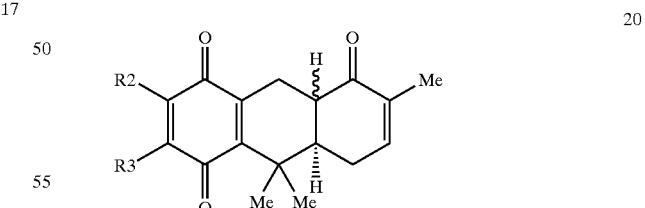

19

6,9,9,10a-Tetramethyl-8a,9,10,10a-tetrahydro-8H-anthracene-1,4,5-trione where $R_2=R_3=H$ or a derivative thereof where $R_2$, and $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH—, N-dialkyl wherein the alkyl groups are the same or different, or a methylenedioxy group is fused in lieu of $R_2$, $R_3$ position; or a salt thereof.

23. A compound according to claim 2 of formula (20)

20

6,9,9-Trimethyl-8a,9,10,10a-tetrahydro-8H-anthracene-1,4,5-trione where $R_2=R_3=H$ or a derivative thereof where $R_2$, and $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl, N-dialkyl wherein the alkyl groups are the same or different, or a methylenedioxy group fused in lieu of $R_2$, $R_3$ position; or a salt thereof.

24. A compound according to claim 2 of formula (21)

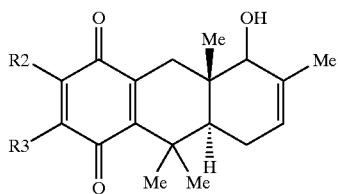

5-Hydroxy-6,9,9,10a-tetramethyl-5,8,8a,9,10,10a-hexahydro-anthracene-1,4-dione trione where $R_2$=$R_3$=H or a derivative thereof where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl, N-dialkyl wherein the alkyl groups are the same or different, or a methylenedioxy group fused in lieu of $R_2$, $R_3$ position; or a salt thereof.

25. A compound according to claim 2 of formula (22)

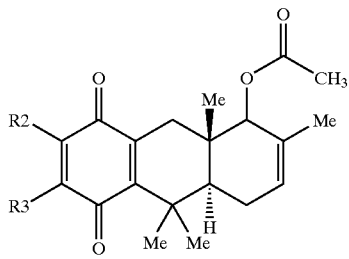

Acetic acid 2,9a,10,10-tetramethyl-5,8-dioxo-1,4,4a,5,8,9,9a,10-octahydro-anthracen-1-yl ester where $R_2$=$R_3$=H or a derivative thereof where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl, N-dialkyl wherein the alkyl groups are the same or different, or a methylenedioxy group fused in lieu of $R_2$, $R_3$ position; or a salt thereof.

26. A compound according to claim 2 of formula (23)

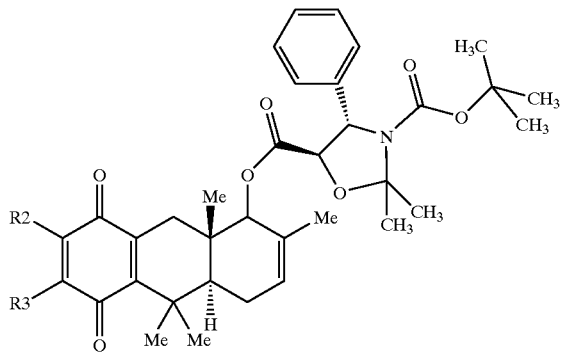

2,2-Dimethyl-4-phenyl-oxazolidine-3,5-dicarboxylic acid 3-tert-butyl ester 5-(2,9a,10,10-tetramethyl-5,8-dioxo-1,4,4a,5,8,9,9a,10-octahydro-anthracen-1-yl) ester where $R_2$=$R_3$=H or a derivative thereof where $R_2$, and $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl, N-dialkyl wherein the alkyl groups are the same or different, or a methylenedioxy group fused in lieu of $R_2$, $R_3$ position; or a salt thereof.

27. A compound according to claim 2 of formula (24)

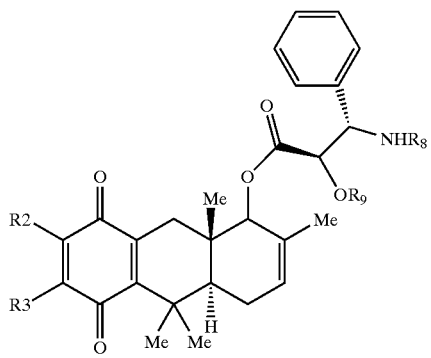

3-Amino-2-hydroxy-3-phenyl-propionic acid 2,9a,10,10-tetramethyl-5,8-dioxo-1,4,4a,5,8,9,9a,10-octahydro-anthracen-1-yl ester where $R_2$=$R_3$=$R_8$=$R_9$=H or a derivative thereof where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl, N-dialkyl wherein the alkyl groups are the same or different, or a methylenedioxy group fused in lieu of $R_2$, $R_3$ position;

$R_8$ is $COCH_3$, $COCF_3$, benzoyl or tert.-butyloxycarbonyl, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl; and $R_9$ is $COCH_3$, $COCF_3$, benzoyl or tert-butyloxycarbonyl or a salt thereof.

28. A compound according to claim 2 of formula (25)

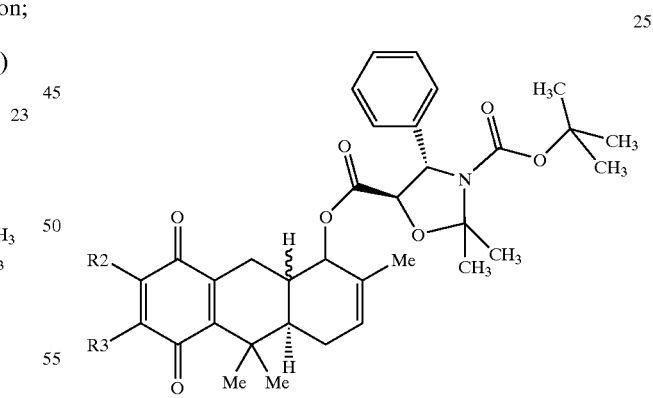

2,2-Dimethyl-4-phenyl-oxazolidine-3,5-dicarboxylic acid 3-tert-butyl ester 5-(2,10,10-trimethyl-5,8-dioxo-1,4,4a,5,8,9,9a,10-octahydro-anthracen-1-yl) ester where $R_2$=$R_3$=H or a derivative thereof where $R_2$, and $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl, N-dialkyl wherein the alkyl groups are the same or different, or a methylenedioxy group fused in lieu of $R_2$, $R_3$ position; or a salt thereof.

29. A compound according to claim 2 of formula (26)

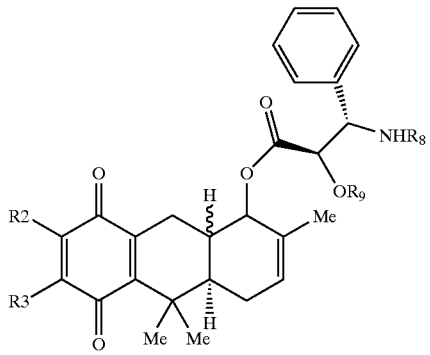

3-Amino-2-hydroxy-3-phenyl-propionic acid 2,10,10-trimethyl-5,8-dioxo-1,4,4a,5,8,9,9a,10-octahydro-anthracen-1-yl ester where $R_2=R_3=R_8=R_9=H$ or a derivative thereof where $R_2$, and $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl, N-dialkyl wherein the alkyl groups are the same or different, or a methylenedioxy group is fused in lieu of $R_2$, $R_3$ position;

$R_8$ is $COCH_3$, $COCF_3$, benzoyl or tert.-butyloxycarbonyl, alkyl, 4-methylbutyl, benzyl, isopropyl, 1-hydroxyethyl, 2 or 3 or 4-hydroxybenzyl, 2 or 3 or 4-alkoxybenzyl, 3,4-dihydroxybenzyl, 3,4-dialkoxybenzyl, N-[2-hydroxyethyl]-2-aminoethyl, 3,4-methylenedioxybenzyl, 5-amino-4-hydroxy-2-oxocyclohexyl, 2 or 3 or 4-fluorobenzyl, 3-aminopropyl, 4-aminobutyl or indole-3-methyl; and $R_9$ is $COCH_3$, $COCF_3$, benzoyl or tert.-butyloxycarbonyl or a salt thereof.

30. A compound of formula (32)

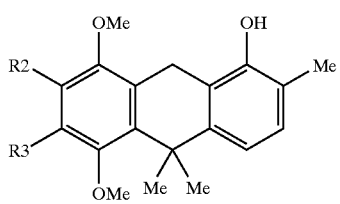

5,8-Dimethoxy-2,10,10-trimethyl-9,10-dihydro-anthracen-1-ol where $R_2=R_3=H$ or a derivative thereof where $R_2$, and $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl, N-dialkyl wherein the alkyl groups are the same or different, or a methylenedioxy group fused in lieu of $R_2$, $R_3$ position; or a salt thereof.

31. A compound according to claim 2 of formula (27)

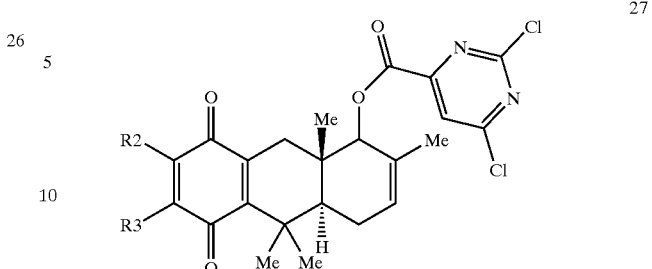

2,6-Dichloro-pyrimidine-4-carboxylicacid-2,9a,10,10-tetramethyl-5,8-dioxo-1,4,4a,5,8,9,9a,10-octahydro-anthracen-1-yl ester where $R_2=R_3=H$ or a derivative thereof where $R_2$, and $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl, N-dialkyl wherein the alkyl groups are the same or different, or a methylenedioxy group fused in lieu of $R_2$, $R_3$ position; or a salt thereof.

32. A compound of formula (31)

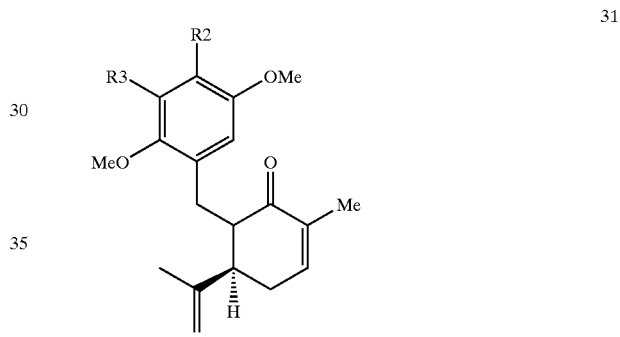

6-(2,5-Dimethoxy-benzyl)-5-isopropenyl-2-methyl-cyclohex-2-enone where $R_2=R_3=H$ or a derivative thereof where $R_2$, $R_3$ are the same or different and represent hydroxy, alkoxy, methoxymethyloxy, alkylthio, amino, alkylamino, dialkylamino, alkylcarbonyloxy, $NHCOCH_3$, $NHCOCF_3$, NH-alkyl, N-dialkyl wherein the alkyl groups may are the same or different, or a methylenedioxy group fused in lieu of $R_2$, $R_3$ position; or a salt thereof.

33. A compound of having formula (34)

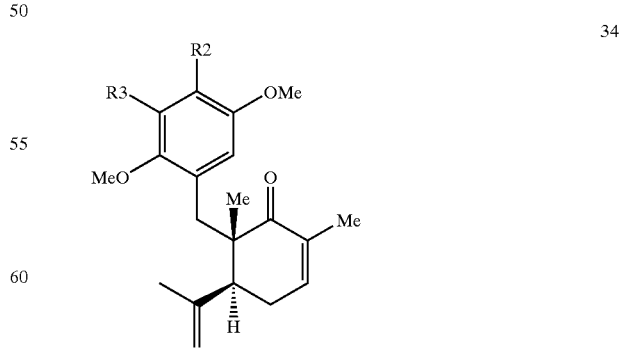

6-(2,5-Dimethoxy-benzyl)-5-isopropenyl-2,6-dimethyl-cyclohex-2-enone where $R_2=R_3=H$ or a derivative thereof where $R_2$, and $R_3$ are the same or different and represent hydroxy, alkoxy, methoxymethyloxy, alkylthio, amino, alkylamino, dialkylamino, alkylcarbonyloxy, NHCOCH$_3$, NHCOCF$_3$, NH-alkyl, N-dialkyl wherein the alkyl groups are the same or different, or a methylenedioxy group fused in lieu of R$_2$, R$_3$ position; or a salt thereof.

34. A method of treating a patient with adenocarcinoma of the colon, pancreas, prostate, lung, larynx, ovary, breast, glioblastoma, oral cavity, endothelial cells or leukemia comprising administering an effective amount of hydroanthracene based compounds as claimed in any one of the claims 1 to 29 or 31 to the patient in need thereof.

35. A composition comprising a hydroanthracene based compound of claim 1 and a pharmaceutically acceptable additive, diluent, excipient, solvent, binder, stabilizer, carrier, filler or lubricant.

36. A composition as claimed in claim 35 which provides 0.1 to 10 gram per unit dose of hydroanthracene based compound.

37. A method as claimed in claim 34 wherein said patient is a human, mammal or other animal.

38. A method as claimed in claim 34 wherein the hydroanthracene based compound is administered in the form of a tablet, lozenge, capsule, powder, aqueous or oily suspension, syrup, elixir, implant or aqueous solution.

39. A method as claimed in claim 34 wherein the dosage for humans is in the range of 1 mg/Kg. B. Wt to 300 mg/Kg. B. Wt.

40. A method as claimed in claim 34 wherein the hydroanthracene based compound is administered to the patient systemically.

41. The hydroanthracene based compound according to any one of claims 1 to 3, wherein the alkyl of NH-alkyl is selected from the group consisting of methyl, propyl, butyl and t-butyl.

42. The hydroanthracene based compound according to any one of claims 1 to 3, wherein the alkyl group of NH-dialkyl are selected from the group consisting of methyl, ethyl, propyl, butyl and t-butyl.

43. The compound according to anyone of claims 1 to 3 wherein the aryl of NH-aryl is phenyl, 2 or 3 or 4-alkoxyphenyl, 2 or 3 or 4-fluorophenyl, 2 or 3 or 4-bromophenyl, 2,3 or 2,4 or 3,4 or 3,5-dialkoxyphenyl.

44. The compound according to anyone of claims 1 to 3 wherein the aryl of NH-aryl is phenyl, 2 or 3 or 4-alkoxyphenyl, 2 or 3 or 4-fluorophenyl, 2 or 3 or 4-bromophenyl, 2,3 or 2,4 or 3,4 or 3,5-dialkoxyphenyl.

45. A method of treating a patient with adenocarcinoma of the colon, pancreas, prostate, lung, larynx, ovary, breast, glioblastoma, oral cavity, endothelial cells or leukemia comprising administering an effective amount of hydroanthracene based compounds as claimed in anyone of claims 41 to 44 to the patient in need thereof.

46. A composition comprising a hydroanthracene based compound of claim 2 and a pharmaceutically acceptable additive, diluent, excipient, solvent, binder, stabilizer, carrier, filler or lubricant.

47. A composition comprising a hydroanthracene based compound of claim 3 and a pharmaceutically acceptable additive, diluent, excipient, solvent, binder, stabilizer, carrier, filler or lubricant.

48. A method of treating a patient with adenocarcinoma of the colon, pancreas, prostate, lung, larynx, ovary, breast, glioblastoma, oral cavity, endothelial cells or leukemia comprising administering an effective amount of hydroanthracene based compounds as claimed in anyone of claims 35, 46 or 47 to the patient in need thereof.

* * * * *